(12) United States Patent
Simpson et al.

(10) Patent No.: US 7,354,750 B2
(45) Date of Patent: Apr. 8, 2008

(54) METHODS FOR SEPARATING MOLECULES

(75) Inventors: Daniel J. Simpson, Middleton, WI (US); Tonny Johnson, Madison, WI (US); John Shultz, Verona, WI (US); Roderick G. Flemming, McFarland, WI (US); Rebecca Godat, DeForest, WI (US); Sanchayita Kar, Madison, WI (US); Robin Hurst, Madison, WI (US)

(73) Assignee: Promega Corporation, Madison, WI (US)

( * ) Notice: Subject to any disclaimer, the term of this patent is extended or adjusted under 35 U.S.C. 154(b) by 725 days.

(21) Appl. No.: 10/689,368

(22) Filed: Oct. 20, 2003

(65) Prior Publication Data
US 2004/0185545 A1    Sep. 23, 2004

Related U.S. Application Data

(60) Provisional application No. 60/419,614, filed on Oct. 18, 2002.

(51) Int. Cl.
C12N 11/00 (2006.01)
B01J 20/22 (2006.01)
B01J 20/10 (2006.01)
B01J 20/283 (2006.01)
B01J 29/04 (2006.01)

(52) U.S. Cl. ............... 435/183; 435/174; 435/176; 435/178; 435/180; 435/182; 435/188; 502/401; 502/402; 502/405; 502/407; 502/408; 502/415; 502/62; 502/63; 502/85; 502/87

(58) Field of Classification Search ............... 502/407
See application file for complete search history.

(56) References Cited

U.S. PATENT DOCUMENTS

| 3,621,018 A | 11/1971 | Hindersinn et al. |
| 4,080,171 A | 3/1978 | Sano et al. |
| 4,220,726 A | 9/1980 | Warshawsky |
| 4,238,328 A | 12/1980 | Bowes et al. |
| 4,500,494 A | 2/1985 | Scher |
| 5,047,513 A | 9/1991 | Döbeli et al. |
| 5,175,271 A | 12/1992 | Thomas et al. |

(Continued)

FOREIGN PATENT DOCUMENTS

WO    WO 91/12079    8/1991

(Continued)

OTHER PUBLICATIONS

Frenzel, et al. "Novel purification system for 6xHis-tagged proteins by magnetic affinity separation" *Journal of Chromatography B*, 793 (2003) 325-329.

(Continued)

*Primary Examiner*—Joseph D. Anthony
(74) *Attorney, Agent, or Firm*—Michael Best & Friedrich LLP

(57) ABSTRACT

The present invention provides compositions and methods for the separation of metals or molecules such as polypeptides, nucleic acids, or endotoxins using a metal-modified solid support. The metals or molecules are isolated from a starting material using the modified solid supports of the invention. Also provided by the invention are kits that can be used in connection with the inventive methods.

24 Claims, 31 Drawing Sheets

U.S. PATENT DOCUMENTS

| | | | |
|---|---|---|---|
| 5,217,866 | A | 6/1993 | Summerton et al. |
| 5,250,188 | A | 10/1993 | Bruening et al. |
| 5,922,545 | A | 7/1999 | Mattheakis et al. |
| 5,932,102 | A | 8/1999 | Wyllie et al. |
| 5,981,194 | A | 11/1999 | Jefferies et al. |
| 6,106,724 | A | 8/2000 | McCulloch et al. |
| 6,194,550 | B1 | 2/2001 | Gold et al. |
| 6,207,446 | B1 | 5/2001 | Szostak et al. |
| 6,242,581 | B1 | 6/2001 | Nelson et al. |
| 6,296,937 | B2 | 10/2001 | Pryor et al. |
| 6,379,970 | B1 | 4/2002 | Liebler et al. |
| 6,428,807 | B1 | 8/2002 | MacFarlan et al. |
| 6,441,009 | B1 | 8/2002 | Fernandez-Pol |
| 6,479,300 | B1 | 11/2002 | Jiang et al. |
| 2001/0021535 | A1 | 9/2001 | Nelson et al. |
| 2001/0039014 | A1 | 11/2001 | Bass et al. |
| 2001/0046680 | A1 | 11/2001 | Yu |
| 2002/0019496 | A1 | 2/2002 | Pevow |
| 2002/0037532 | A1 | 3/2002 | Regnier et al. |
| 2002/0040275 | A1 | 4/2002 | Cravatt et al. |
| 2002/0058269 | A1 | 5/2002 | Nock et al. |
| 2002/0182651 | A1 | 12/2002 | Patricelli |

FOREIGN PATENT DOCUMENTS

| | | |
|---|---|---|
| WO | WO 00/11208 | 3/2000 |
| WO | WO 02/37100 | 5/2002 |
| WO | WO 02/42398 A2 | 5/2002 |

OTHER PUBLICATIONS

Altin, et al., *Biochim. Biophys. Acta*, Aug. 6;1513(2):131-48 (2001).
Barret, et al., *Anal. Chem.*, 73: 5232 (2001).
Brandt, et al., *Bioconjug. Chem.*, Mar-Apr.;3(2):118-25 (1992).
Coulet, et al. "Immobilization of enzymes on metal-chelate regenerable carriers" *Biotechnology and Bioengineering*, 23: 663-668 (1981).
Erdogan & Houslay, *Biochem. J.*, 321: 165-175 (1997).
Fornasiero, et al., *Invest. Radio.*, Apr.;22(4): 322-7 (1987).
Frelinger, et al., *Biotechniques*, Nov.;31 (5): 1194 (2001).
Fujihara, et al., *Genes Cells*, Mar.;7(3): 343-50 (2002).
Gavin, et al., *Nature*, 415(6868): 141-147 (2002).
Gerber, et al., *Anal. Chem.*, 73: 1651 (2001).
Giriat et al., *Genet. Eng.*, (NY), 23: 171-199 (2001).
Goubran-Botros, et al., *Biochem. Biophys. Acta*, May24;1074(1): 69-73 (1991).
Goubran-Botros, et al., *J. Chromotogr.*, Apr24;597(1-2):357-64 (1992).
Hainfeld, et al., *J. Struct. Biol.*, Sep;127(2):185-98 (1999).
Haupt, Karsten, et al., *Anal. Biochem.*, Feb15;234(2):149-54 (1996).
He, Mingyue, *Nucleic Acids Res.*, Aug 1;29(15):E73-3 (2001).
Hermason, Greg T., Mallia, Krishna; Smith; Paul K., *Immobilized Affinity Legand Techniques* Academic Press (1992).
Hochuli, et al., *J. Chromatogr.*, 411, 177-184 (1987).
Ito, et al., *J. Biol. Chem.*, 274, 9029-9037 (1999).
Kapanidis, et al., *J. Am Chem Soc*, Dec5;123(48):12123-5 (2001).
Kurt-Othmer Encyclopedia of Chemical Technology, vol. 21, 4th ed., Mary Howe-Grant, ed., John Wiley & Sons, p. 1021 (1997).
Laboureau, et al. *J. Mol. Recognit.* Nov-Dec;10(6):262-8 (1997).
Lamla, Thorsten, *FEBS Lett*, Jul27;502(1-2):35-40 (2001).
Maniatis, et al. Ausubel, Molecular Cloning, Cold Spring Harbor Laboratory (1982).
Motekaitis, et al., "New multidentate ligands. XV. Chelating tendencies of diglycine-N,N-diacetic acid, triglycine-N,N-diacetic acid, and tetraglycine-N,N-diacetic acid", *Inorganic Chemistry*, 13(3) 550-9 (1974).
Murata, et al., *Anal. Sci.* Mar; 17(3):387-90 (2001).
Nanak, et al., *J. Mol Recognit.*, Jan-Apr;8(1-2):77-84 (1995).
Porath, et al., *Nature*, 258, 598-599 (1975).
Principles of Gene Manipulation, Old and Primrose, 2nd ed., (1981).
Proffitt, et al., *J, Nucl, Med.*, Jan;24(1):45-51 (1983).
Robert & Smith, *Curr, Opin, Chem, Biol,*, 6(3): 375-383 (2002).
Thess, et al., *J. Biol Chem.*, electronically published (Jul. 11, 2002).
Vosters, et al., *Protein Expr. and Purif.*, 3, 18-26 (1992).
Xu, et al., *Proc. Natl. Acad. Sci. USA*, 96, 151-156 (1999).
Zhu, Heng, et al., *Science*, Sep14;293(5537):2101-5 (2001).

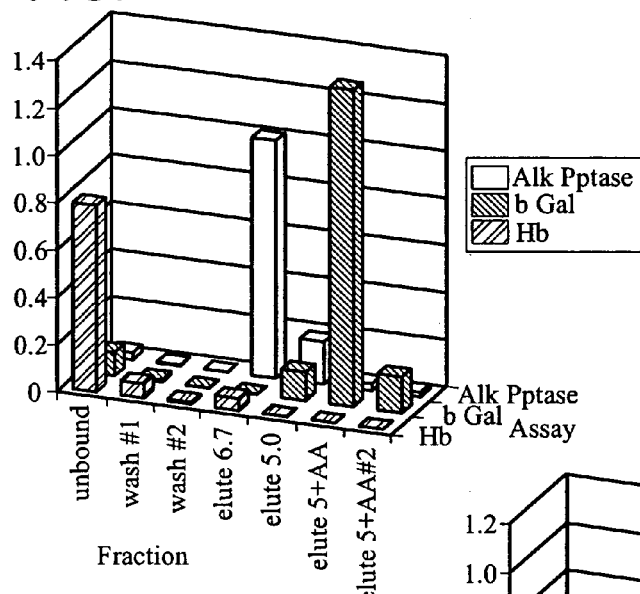
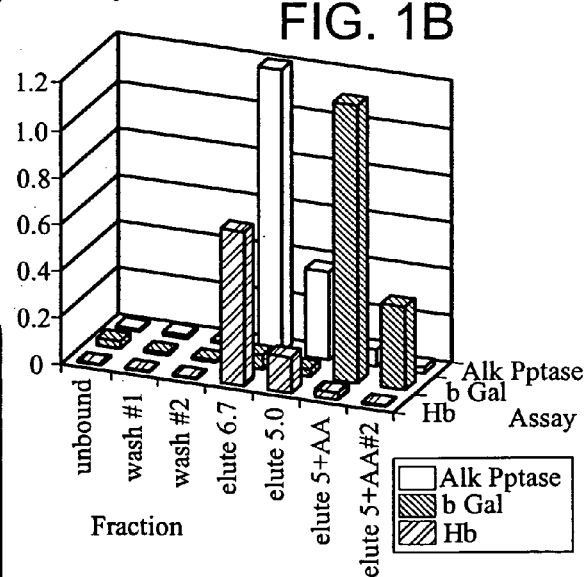
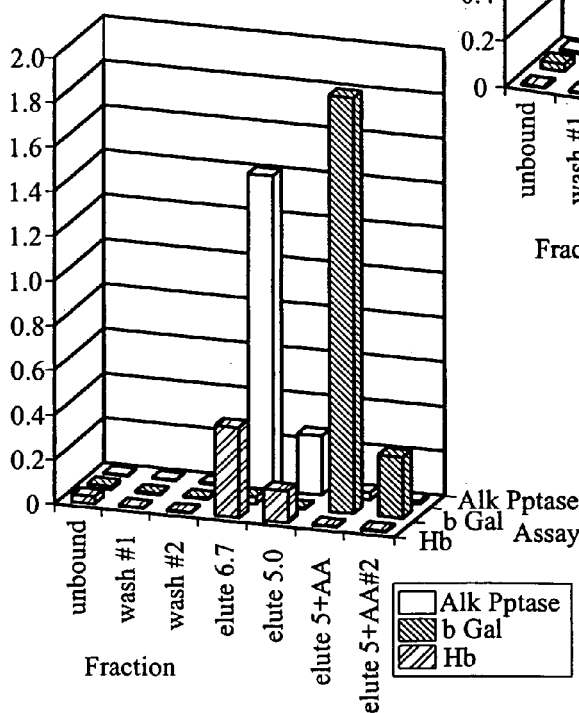
FIG. 1A, FIG. 1B, FIG. 1C — Protein Fractionation on Various Resins

Purification of His-RNaseHI on Nickel NTA-Modified Silica Magnetic Particles

Purification and Separation of Hemoglobin

— hemoglobin

Lanes 1: Control lysate (before teatment)
2: Molecular weight markers
3: Nickel 100mM imidazole elution
4: Copper 100mM imidazole elution
5: Cobalt 100mM imidazole elution
6: Zinc 100mM imidazole elution
7: Nickel 500mM imidazole elution
8: Copper 500mM imidazole elution
9: Cobalt 500mM imidazole elution
10: Zinc 500mM imidazole elution

Purification of His-RNaseHI

500mM imidazole elution

B = Blank
P = Purified his-methionyl tRNA synthetase
M = Particle attached his-methionyl tRNA synthetase 1   2   3   4   5   6   7   8   9   10

B. Protein concentration

C. Rabbit reticulocyte lysate (RRL) control
1. 3 µl RRL flow through
5. 5 µl RRL flow through
10. 10 µl RRL flow through
20. 20 µl RRL flow through
1. 1 µl RRL elute
5. 5 µl RRL elute
10. 10 µl RRL elute
20. 20 µl RRL elute B. Protein concentration C. CHO cell lysate control
1. 3 μl CHO cell lysate flow through
5. 5 μl CHO cell lysate flow through
10. 10 μl CHO cell lysate flow through
20. 20 μl CHO cell lysate flow through
1. 1 μl CHO cell lysate elute
5. 5 μl CHO cell lysate elute
10. 10 μl CHO cell lysate elute

FIG. 18A 1   2   3   4   5 6   7   8   9

Fig. A. Binding and elution of complex mixture of proteins from copper-MagneSil particles Lanes: 
1. Wheat germ lysate control
2. 3 μl wheat germ lysate flow through
3. Marker
4. 5μl wheat germ lysate flow through
5. 10μl wheat germ lysate flow through
6. 20 μl wheat germ lysate low through
7. 1 μl wheat germ lysate elute
8. 5μl wheat germ lysate elute
9. 10μl wheat germ lysate elute

B. Protein concentration

C. wheat germ lysate control
1. 3 µl wheat germ lysate flow through
5. 5 µl wheat germ lysate flow through
10. 10 µl wheat germ lysate flow through
20. 20 µl CHO cell lysate flow through
1. 1 µl wheat germ lysate elute
5. 5 µl wheat germ lysate elute
10. 10 µl wheat germ lysate elute Lanes: 1. Eluted with 100 mM imidazole
2. Eluted with 200 mM imidazole
3. Marker
4. Eluted with 500 mM imidazole
5. Eluted with 1M imidazole
6. Eluted with pH 8.5 ammonium acetate
7. Eluted with pH 9.5 ammonium acetate
8. Eluted with pH 10.5 ammonium acetate
9. Eluted with pH 12.5 ammonium acetate Lanes: 1. Molecular weight markers
2. Eluted with pH 8.5 ammonium acetate
3. Eluted with pH 9.5 ammonium acetate
4. Eluted with pH 10.5 ammonium acetate
5. Eluted with pH 12.5 ammonium acetate
6. Eluted with 0.05% TFA
7. Eluted with 0.1% TFA
8. Eluted with 1.0% TFA Lanes 1: Marker
2: Control ovalbumin
3: NTA-magnetic silica flow through
4: Nickel-magnetic silica flow through
5: Fe+++-magnetic silica flow through
6: Ga+++-magnetic silica flow through
7: NTA-magnetic silica elute
8: Nickel-magnetic silica elute
9: Fe+++-magnetic silica elute
10: Ga+++-magnetic silica elute 1. Control retic lysate
2. NTA-magnetic silica FT
3. $Ni^{2+}$-magnetic silica FT
4. Marker
5. $Ga^{3+}$-magnetic silica FT
6. $Fe^{2+}$-magnetic silica FT
7. NTA-magnetic silica 2% $NH_4OH$ eluant
8. $Ni^{2+}$-magnetic silica a 2% $NH_4OH$ eluant
9. $Ga^{3+}$-magnetic silica a 2% $NH_4OH$ eluant
10. $Fe^{3+}$-magnetic silica a 2% $NH_4OH$ eluant

FIG. 23A
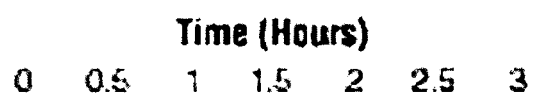

1 2 3 4

//METHODS FOR SEPARATING MOLECULES

CROSS-REFERENCE TO RELATED APPLICATIONS

This application claims priority to U.S. Provisional Application No. 60/419,614, filed Oct. 18, 2002.

STATEMENT REGARDING FEDERALLY SPONSORED RESEARCH OR DEVELOPMENT

Not applicable.

BACKGROUND OF THE INVENTION

The present invention relates broadly to compositions and methods for separating metal ions or other target material, including, but not limited to, polypeptides, nucleic acids, or endotoxins, from non-target material.

SUMMARY OF THE INVENTION

In one aspect, the invention includes methods for isolating target material from a starting material comprising contacting the starting material with a composition selected from the group consisting of:

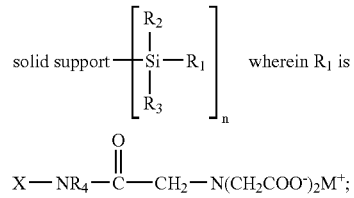

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, a thiol, an amine, a silanol bond to the solid support, a bond to another silane ligand, or $O$—Si—$Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an integer >1; and

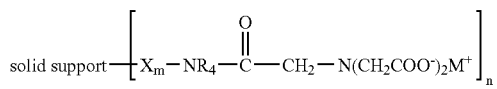

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

$M^+$ is a metal ion;

n is an integer $\geq 1$; and m is 0 or 1;

to form a complex between at least a portion of the target material and the composition.

These and other aspects of the present invention will be better appreciated by reference to the following drawings and Detailed Description.

Each of the publications or patent applications cited herein is incorporated by reference in its entirety. In the case of conflict between the present disclosure and an incorporated publication, the present disclosure should control.

BRIEF DESCRIPTION OF THE DRAWINGS

FIG. 1 provides graphs comparing fractionation of hemoglobin, alkaline phosphatase, and B-galactosidase on aminopropyl-modified magnetic silica particles (FIG. 1A), Q-sepharose resin (FIG. 1B), and DEAE resin (FIG. 1C).

FIG. 18A is an SDS-PAGE gel illustrating the binding and elution patterns of complex protein mixtures from wheat germ cell lysate using copper 3-[[[bis(carboxymethyl)amino]-acetyl]amino]-propyl magnetic silica particles.

DETAILED DESCRIPTION OF THE INVENTION

Figure 2:
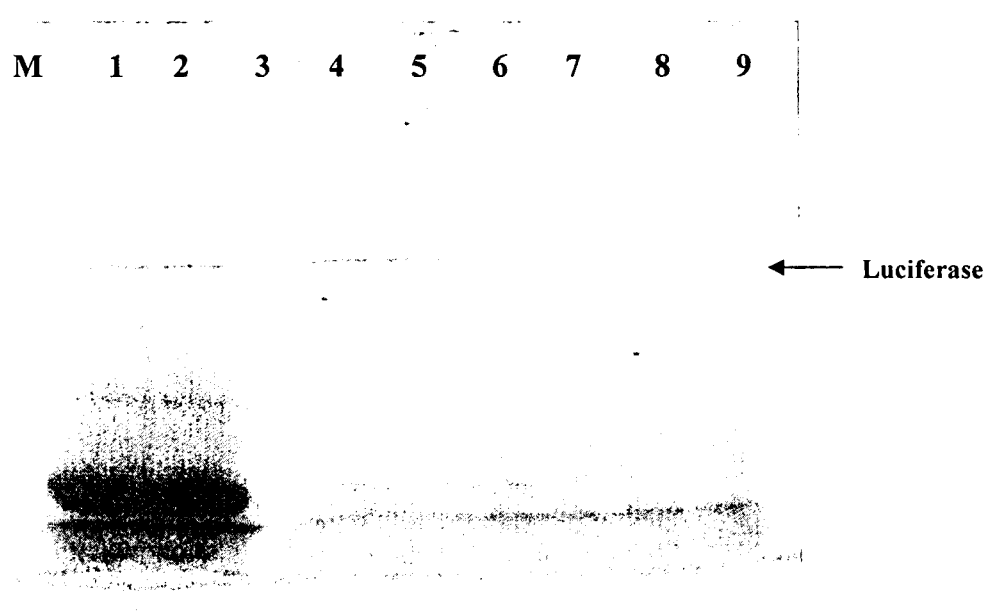
FIG. 2 is an SDS-PAGE gel of FluoroTect-Green labeled luciferase and hemoglobin fractionated using aminopropyl-modified magnetic silica particles.

The present invention provides compositions and methods for separating target material from a starting material. Suitable target material includes, but is not limited to, metal ions, polypeptides, nucleic acids, whole cells, cell membranes, and the like. The invention also provides kits suitable for use in the practice of the methods of the invention.

The compositions and methods of the invention are useful in a wide variety of applications, including, for example, fractionation of molecules in a mixture, removing metal ions from a fluid, capturing cells from a cell suspension, isolating membranes or membrane proteins, removing undesired contaminating proteins from a mixture, and the like. As one skilled in the art will appreciate, the compositions and methods of the invention may be used alone, or in conjunction with other compositions or methods.

Because the compositions and methods of the invention permit facile isolation or purification of target material, they are susceptible to miniaturization, robotic manipulation, and use in high throughput assays. The compositions and the methods of the present invention are also suitable for use in structural and functional genomics, or proteomics.

The compositions of the present invention comprise modified solid supports, including nitrilotriacetic acid (NTA)-modified solid supports and metal-modified solid supports.

The methods of the invention employ NTA-modified solid supports, metal-modified solid supports, or amine-modified solid supports to form a complex with, or otherwise effect separation of, a target material such as metal ions, molecules, subcellular components, or whole cells, from non-target material in a starting material.

Suitable solid supports for making the modified solid supports of the present invention include, without limitation, gels or hard support material, agarose, polyacrylamide, cellulose, plastics, polysaccharides, nylon, polystyrene, latex methacrylate, silica, aluminum oxide, electrodes, membranes, and derivatives thereof.

Suitable silica solid supports include, but are not limited to, siliceous oxide, magnetic silica particles, solid silica such as glass or diatomaceous earth and the like, or a combinations of silica materials (see, e.g., preparation of silica discussion in Kurt-Othmer Encyclopedia of Chemical Technology, Vol. 21, 4th ed., Mary Howe-Grant, ed., John Wiley & Sons, pub., 1997, p. 1021). As discussed in the examples below, suitable silica gels are available commercially from suppliers such as Silicycle (Quebec City, Canada), J. T. Baker (Phillipsberg, N.J.), and Sigma-Aldrich, (St. Louis, Mo.). Suitable silica gels for the compositions and methods of the invention are further described in the examples below. Other suitable silica supports include crystalline or vitreous silicas, such as quartz, vitreous silica, controlled pore glass particles, and glass fibers.

Silica gel may be characterized by pore diameter, particle size, or specific surface area. Suitable silica gels have a pore diameter from about 30 to about 1000 Angstroms, a particle size from about 2 to about 300 microns, and a specific surface area from about 50 $m^2/g$ to about 1000 $m^2/g$. Suitable silica gels include, for example, those having a pore diameter of about 40 Angstroms, about 60 Angstroms, and about 150 Angstroms; those having a particle size of about 2 to about 25 microns, about 5 to about 25 microns, about 15 microns, about 63 to about 200 microns and about 75 to about 200 microns; and those having a specific surface area of about 300 $m^2/g$, about 500 $m^2/g$, about 550 $m^2/g$, about 675 $m^2/g$, and about 750 $m^2/g$.

Conveniently, a solid support according to the present invention may comprise magnetic silica particles. Magnetic silica particles comprise a superparamagnetic core coated with a hydrous siliceous oxide adsorptive surface (i.e. a surface having silanol or Si—OH groups). Suitable, commercially available magnetic silica particles include MagneSil™ particles available from Promega Corporation (Madison, Wis.). The preparation of magnetic silica particles suitable for use as a support according to the present invention is described in U.S. Pat. No. 6,296,937.

Suitable cellulose supports include, but are not limited to, nitrocellulose and cellulose acetate.

Suitable membranes include, but are not limited to, glass fiber membranes impregnated with silica.

Suitable aluminum oxide solid supports include, but are not limited to, Brockmann aluminum oxides that are about 150 mesh and 58 angstroms.

An amine-modified solid support, as described herein, may be formed, for example, using a solid support that includes at least one free hydroxyl group such that, when the solid support is contacted with an aminosilane compound, the silicon atom of the aminosilane compound is covalently bound to the solid support by at least one silanol bond to form an amine-modified solid support.

Aminosilane compounds are commercially available through suppliers such as United Chemical Technologies, Inc. (Bristol, Pa.). Suitable aminosilane compounds comprise

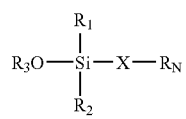

wherein X is an alkylene moiety of up to 20 carbon atoms that may be saturated, unsaturated, branched, linear, or cyclic, for example, methylene, ethylene propylene, nonylene, or an aralkylene moiety of up to 20 carbon atoms in which the alkyl portion may be saturated, unsaturated, branched, linear, or cyclic or an arylene moiety of up to 20 carbon atoms, and wherein X may be unsubstituted or substituted as defined below with respect to hydrocarbon moiety;

$R_1$ is a hydrocarbon moiety, or a substituted hydrocarbon moiety;

$R_2$ and $R_3$ are independently selected from $R_1$, a hydrocarbon moiety, a substituted hydrocarbon moiety, a halogen atom, a hydrogen atom, a hydroxy, a thiol, an amine, a silanol bond to the solid support, a bond to another silane ligand, or O—Si—$Y_1Y_2Y_3$, wherein $Y_1$, $Y_2$ and $Y_3$ are independently selected from a hydrocarbon moiety, or a substituted hydrocarbon moiety; and $R_N$ is $NH_2$, $NHR_{N1}$, $NR_{N1}R_{N2}$, or $NR_{N1}R_{N2}R_{N3}$, wherein $R_{N1}$, $R_{N2}$, and $R_{N3}$ are independently selected from a hydrocarbon moiety, a substituted hydrocarbon moiety, or a hydrogen atom; suitably $R_{N1}$, $R_{N2}$, and $R_{N3}$ may independently be an alkyl moiety of up to six carbon atoms in a longest chain, a substituted alkyl moiety of up to six carbon atoms in a longest chain, or a hydrogen atom. A "longest chain" is the longest chain of an alkyl moiety as utilized in IUPAC nomenclature.

The term "hydrocarbon moiety" as used herein refers to an alkyl group of up to 20 carbon atoms (i.e., alkanes, alkenes or alkynes) that may be saturated, unsaturated, branched, linear, or cyclic; or an aralkyl group of up to 20 carbon atoms in which the alkyl portion may be saturated, unsaturated, branched, linear or cyclic; or an aryl group of up to 20 carbon atoms. Suitably, the hydrocarbon moiety has from 2 to 15 carbon atoms, or from 5 to 10 carbon atoms. A "substituted hydrocarbon moiety" refers to a hydrocarbon moiety, as defined herein, in which at least one carbon atom is substituted with an oxygen, a sulfur, or a nitrogen atom. The substituent may be, for example, oxo, alkoxy, alkoxycarbonyl, hydroxy, esters, thioethers, amino, alkylamine, or carbamoyl.

Examples of suitable aminosilane compounds useful in the practice of the present invention include, but are not limited, to aminopropylsilane, propylethylenediaminesilane, N-[3-(trimethoxysilyl)propyl]ethylenediamine, and N-[3-(trimethoxysilyl)propyl] diethylenetriamine.

An NTA-modified solid support, as described herein, may be produced by contacting a solid support having a free —$NH_2$ moiety to form an amide bond between nitrilotriaceticacid and the amine group of the support. Nitrilotriacetic acid acts as a chelating agent capable of forming stable complexes with polyvalent metal ions.

Any solid support is acceptable for use in the production of an NTA-modified solid support, provided that it has an amine moiety that can be modified, or that the solid support can be made to contain a modifiable amine group. Suitable solid supports for use in the manufacture of NTA-modified solid supports have a plurality of free $NH_2$ moieties. One skilled in the art would be able to attach a free amine functionality to a solid support by chemically modifying the surface of the solid support. See, e.g., Greg T. Hermason, A. Krishna Mallia, Paul K. Smith, *Immobilized Affinity Legand Techniques*, Academic Press (1992). In addition, suitable solid supports with free $NH_2$ moieties capable of binding to the NTA to form an NTA-modified solid support according to the present invention are commercially available. These include, but are not limited to, agarose-based supports sold by Sigma-Aldrich Inc. (St. Louis, Mo.); latex-based supports sold by International Dynamics Corporation, (Longwood, Fla.); polystyrene-based supports sold by Bangs Laboratories Inc., (Fishers, Ind.); Spherotech, (Libertyville, Ill.); and Dynal Biotech, (Lake Success, N.Y.).

In another aspect, the present invention provides metal-modified solid supports. The metal-modified solid support, as described herein, may be produced by contacting the NTA-modified solid support described above with a metal ion solution to form the metal-modified solid support. The metal ion solution may be comprised of metal ion salts, wherein the salts include, but are not limited to chloride, sulfate, phosphate, acetate, carbonate, citrate, acetylacetonate, bromide, fluoride, iodide, nitrate and oxalate salts. The metal concentration may be from less than about $10^{-6}$ M to about 1 M. Typically, the metal ion concentration in solution may be in the range of about 0.1 M to about 1 M. It is envisioned that the metal ion solution may be composed of only one metal ion or a mixture of different metals. Suitably, a tetradentate complex may be formed between the metal ion and the NTA-modified solid support. See, e.g., *New multidentate ligands. XV. Chelating tendencies of diglycine-N,N-diacetic acid, triglycine-N,N-diacetic acid, and tetraglycine-N,N-diacetic acid*, Inorganic Chemistry (1974), 13(3), 550-9.

By a "metal ion" as it is used in the context of a metal-modified solid support, it is meant any metal with a oxidation state between +1 and +6. Suitably, the metal may be nickel, copper, cobalt, iron, zinc, or gallium. Additionally the following metal ions are considered suitable for the present invention: iron (III), copper (II), cobalt (II), nickel (II), zinc (II), cerium (III), magnesium (II), calcium (II), galium (III), chromium (III), indium (III), lanthanum (III), lutetium (III), scandium (III), thallium (III), ytterbium (III), thorium (IV), uranate (II) silver (I), gold (I) and copper (I). One skilled in the art would be able to select a suitable metal depending on the material to be separated. Also, it is envisioned that the bound metal ions may be stripped from the metal-modified support with a chelating agent, such as ethylene diamine tetraacetic acid (EDTA), therefore allowing the regeneration of the NTA-modified solid supports.

The modified solid supports of the invention are useful in a number of methods, including, but not limited to, those described in the Examples or in other sections of the specification. As one skilled in the art will appreciate, the supports of the invention may be supplied or used in a variety of different forms, depending on particular requirements of the application. For example, the modified solid supports may be used in a column, a spin column, in wells of a microtiter plate, incorporated into or formed as a filter, as a device implantable in a mammal, or disposed in a transfer means (e.g., a pipet tip).

Starting material used in the methods of the invention may include any material comprising, or suspected of comprising, target material, and may optionally comprise non-target material. Starting material includes material taken directly from a biological source (e.g., a cell culture, spent culture medium, or a cell lysate) or an environmental source (e.g., water or air) as well as material that has been processed or partially purified. Starting material may include the target or non-target material in any form (e.g., in solution or in suspension). The starting material may be derived from eukaryotic or prokaryotic sources, including cultured eukaryotic or prokaryotic cells, and may include either recombinant or naturally occurring biomolecules. The starting material may include, for example, a crude cell lysate, including lysates used in expressions systems, including, but not limited to, cell-free lysates such as *E. coli* S-30, wheat germ, and rabbit reticulocyte lysate. The starting material may be spent bacterial or cell culture medium into which target materials were secreted. A suitable starting material may include a complex mixture of proteins. The starting material may include bacterial, yeast, fungal, or viral material, plant or animal material, including products thereof (e.g., whole blood, plasma, serum, milk, and the like). The starting material may also include fluids such as water, air, or urine.

In the methods of the invention, a starting material is contacted with a modified solid support of the invention to form a complex between a target material and the support. For the sake of simplicity, the material recovered by mechanical separation of the contacted starting material from the particles will be referred to as "flow through", regardless of the means by which separation was effected.

The methods of the present invention depend on the ability of target or non-target material in starting material to complex with a composition of the invention to achieve a particular effect, i.e., a change in the spatial relationship between the target material and the starting material, or a component thereof. This effect may be described, with reference to a target or non-target material, as removing, separating, isolating, purifying, fractionating, or the like. These terms are not intended to limit the invention. One of skill in the art will appreciate that the terms are relative, rather than absolute, and may be used interchangably.

In some applications, the method of the invention is performed in order to effect removal of an undesired target material from a starting material (e.g., removal of potentially toxic metal ions from a fluid such as water). In other cases, the object is to isolate or purify a particular target material from a complex mixture comprising the target material and non-target material, or to fractionate target and non-target material.

Target material such as polypeptides isolated or purified by the method of the present invention are suitable for use in many downstream applications. Further isolation, characterization, or quantitation of isolated target material may be performed by any of a variety of techniques, including, but are not limited to, two-dimensional gel electrophoresis, mass spectrometry, X-ray diffraction, nuclear magnetic resonance, protein chips (array-based or matrix-based), and yeast two-hybrid system.

The term polypeptide as used herein includes a polymer of three or more amino acid units linked via peptide bonds, and may include proteins. Polypeptides may include a single chain, or two or more homologous or heterologous polypeptide chains, as in the case of native proteins have multiple subunits, or in the case of diverse polypeptides that interact or complex with each other (e.g., antibody-antigen complexes, or enzymes that have a protein as a substrate). Polypeptides may include either denatured proteins or native proteins. Suitable polypeptides may include metal binding moieties or surface-active amino acids that can act as electron density donors or acceptors (e.g., lysine, arginine, histidine, cysteine, glutamic acid, or aspartic acid). A polypeptide having greater than three histidine or cysteine residues on its surfaces is particularly well suited for purification according to the methods of the instant invention. The histidines or cysteines may be naturally-occurring histidines (e.g., as found in hemoglobin, myoglobin, and other heme-containing proteins), or may be added to the polypeptide through genetic engineering techniques known to one skilled in the art.

Suitable polypeptides include, without limitation, metallo proteins, hormones, receptors, enzymes, storage polypeptides, blood polypeptides, antibodies, membrane polypeptides, phosphorylated polypeptides, cytoplasmic polypeptides, secretory polypeptides, organelle polypeptides, polypeptide-nucleic acid complexes, multi-protein complexes, mutant polypeptides produced by genetic engineering techniques known to one skilled in the art.

Target material, including target polypeptides, may be modified or designed to include an "affinity tag" to facilitate separation of the target material from non-target material lacking the affinity tag. The affinity-tagged target polypeptide may be formed by chemical or recombinant DNA methods known in the art. Suitably, the affinity tags may be added to the N- or C-terminus, or to both the N- and C-termini, by genetically engineering a polynucleotide sequence encoding the target polypeptide to include the affinity tag. Sequences that encode suitable affinity tags may also be engineered such that affinity tag is at an internal site on the target polypeptide. Suitable affinity tags may include, for example, histidine (His) tags (e.g., polyhistidine tails) and metal binding domains. Other affinity tags suitable for use in the present invention may include poly-arginine tag, Strep-tag, calmodulin binding peptide, maltose binding protein, glutathione-S-transferase (GST), ubiquitine, or biotin/avidin.

The Examples below describe separation of specific his-tagged proteins (e.g, His-luciferase, His-RNaseHI, and His-methionyl tRNA transferase). The methods of the invention were found to be effective in isolating other his-tagged proteins (His-endostatin, His-Tau, His-Karyopherin-alpha 2, His-ubiquitin, His-osteopontin, and His-calcinuerin B alpha proteins) (data not shown). One skilled in the art will appreciate that the methods may be used to purify any his-tagged protein.

It is envisioned that the methods of the invention may be used to isolate any target molecule of interest from non-target molecules in a starting material, provided that the target molecule has a differential tendency to form a complex with the compositions of the invention, relative to at least one species of non-target molecule present in the starting material.

An NTA-modified solid support may be used to remove toxic metals from water, air, blood, or other fluids of interest. For example, the NTA-modified solid may be used to remove and/or recover potentially harmful or toxic metals, such as aluminum, arsenic, bismuth, antimony, excess calcium, excess iron, gold, zinc, magnesium, mercury, cadmium, lead, copper and silver, from industrial waste waters and or from water destined for human consumption. Of particular concern are lead salts that can leach from the pipes and solder joints of home plumbing. The NTA-modified solid supports may be used in a manner similar to chelating agents to remove heavy metal ions from water (e.g., U.S. Pat. No. 4,500,494), to analyze heavy metal ions in water using chelating compounds in conjunction with a filter to trap the metal ions (e.g., U.S. Pat. No. 4,080,171), to purify water (e.g., U.S. Pat. No. 4,348,328), or, in conjunction with a resin, to recover heavy metal ions from liquid (e.g., U.S. Pat. No. 4,220,726).

The NTA-modified solid supports of the present invention may also be useful in a number of other applications in which it is desirable to extract, deactivate or remove metals from fluids, e.g., removing calcium from plasma to convert the plasma to serum, or wiping up spills of radioactive metallic ions in laboratories. The NTA-modified supports may be employed to remove toxic metals from individuals with lead or mercury poisoning.

Interference with or depletion of certain metal ions has been reported as having a role in health conditions. Accordingly, the NTA-modified solid supports of the present invention may be used as a diagnostic tool for detecting and extracting metal-associating molecules indicative of the disease state or predisposition to a disease.

The NTA-modified solid supports may be used to prepare chelating immunostimulating complexes in a manner similar to the general approaches described, for example, in U.S. Pat. No. 6,428,807.

Metal-modified solid supports may be used to separate target material (e.g., polypeptides or nucleic acids) from non-target material in a starting material. For example, the metal-modified support may be used to separate his-tagged polypeptides from other molecules present in a starting material. The starting material may optionally be adjusted to include imidazole in a concentration of from about 0 to about 60 mM. The his-tagged proteins can be eluted from the support using any suitable buffer. A suitable buffer could contain imidazole in a concentration of from about 60 mM to about 1 M. Other suitable elution buffers are those having a pH lower than the isoelectric point (pI) of the protein of interest, suitably less than about pH 5. Other suitable elution buffers include buffers with competing chelating agents such as EDTA or EGTA, trifluoroacetic acid, L-histidine, dipeptides, histidine peptides or polymers, or imidazole-like polymers.

The metal-modified solid support may be used alone or in conjunction with other purification methods, including, for example, methods using an amine-modified solid support.

The metal-modified solid support may also be used to remove endotoxins from a starting material. Suitably, the term endotoxin refers to the lipopolysaccharide complex associated with the outer membrane of certain species of gram-negative bacteria such as *E. coli*, Salmonella, Shigella, Pseudomonas, Neisseria, Haemophilus, or any other endotoxin-producing pathogenic bacterium.

The metal-modified solid support may be used to isolate or identify low-abundance proteins, membrane proteins, or phosphorylated proteins.

The metal-modified support may be used to separate nucleic acids, as described for other IMAC resins in WO 02/42398A2.

As described in the Examples below, the metal-modified solid support of the present invention as well as other solid supports comprising an immobilized metal chelating agent (e.g., nickel agarose beads commercially available from Qiagen) were found to allow detection of proteins complexed to the solid support using a detectable label. In the Examples, Coomassie, fluorescein, or Bodipy were found to complex with proteins immobilized to the solid supports in a quantitative fashion. It is envisioned that any suitable dye or fluorescent label may be used to detect proteins complexed with a solid support comprising an immobilized metal chelating agent. Other examples of suitable detectable labels include, without limitation, remazol brilliant blue R, eosin isothiocyanate, reactive orange, procion red, eosin iodoacetamide, reactive black 5, reactive orange 14, malachite green isothiocyanate, rhodamine isothiocyanate, remasol brilliant violet 5R, rhodamine, and coumarin.

The metal-modified solid support may also be used to isolate or evaluate polypeptide-polypeptide complexes or interactions; screen for polypeptide function; isolating antibodies, antigens, or antibody-antigen complexes; quantitating affinity-tagged polypeptides; diagnostic screening for diseases; antibody screening; antagonist and agonist screening for drugs; reporter gene assays; producing polypeptide expression libraries, producing polypeptide libraries from cells; producing polypeptide microarrays; screening genetically engineered enzymes; co-isolating interacting molecules (e.g., co-factors); reducing in vivo concentrations of an endotoxin; tissue profiling; or cell profiling.

As detailed in the Examples below, amine-modified solid supports were found to be useful in a variety of applications. Amine-modified solid supports permit facile separation of hemoglobin from other materials present in a starting material, isolation of membrane vesicles, purification of membrane proteins, and concentration or purification of cells.

An amine-modified solid support may be used to remove hemoglobin from a starting material. As demonstrated in the Examples below, hemoglobin does not bind to amine-modified silica magnetic particles. Separation of hemoglobin from other proteins may useful in any application in which hemoglobin is present. For example, purification of proteins expressed in a reticulocyte lysate expression system can be enhanced by removing hemoglobin by contacting the lysate with an amine-modified solid support. Removal of hemoglobin is particularly useful in applications employing fluorescent-based detection, because hemoglobin interferes with detection of fluorescently labeled proteins by reducing the signal to noise ratio. In addition to facilitating removal of hemoglobin, the method of the invention may be expected to allow removal of other proteins containing heme groups, such as myoglobin.

An amine-modified solid support may be used to isolate membrane-associated proteins for subsequent identification or characterization. In the examples below, membrane proteins or membrane-associated proteins were expressed in cell-free lysate in presence of microsomal membrane vesicles and separated from other materials present in the lysate by contacting the lysate with an amine-modified solid support such that the membranes formed a complex with the support. This method can be adapted for use in screening collections of in vitro expressed proteins to facilitate isolation and identification of membrane proteins and is suitable for use in high throughput screening of such proteins. As can be seen from the Examples, the method may optionally employ a non-ionic detergent, which facilitates recovery of membrane proteins.

As described in the Examples, an amine-modified solid support may be used in conjunction with other purification methods, such as metal-modified solid supports, to purify molecules of interest, including affinity-tagged polypeptides under denaturing or non-denaturing conditions. The order in which purification steps using amine-modified solid support are performed relative to other steps in a purification scheme may be altered, depending on the nature of the target material and any non-target material that may be present.

It is envisioned that the specific target proteins bound to the amine-modified solid support may be subsequently eluted under appropriate conditions specific to the particular target protein. Suitable fractionation conditions are known to skilled researchers in the art. As shown in the examples, target proteins containing histidine residues, such as a his-tag, do not bind to amine-modified solid supports. It is envisioned that the amine-modified solid supports of the present invention may facilitate separation of target proteins that have been genetically engineered to include moieties that reduce binding to amine-modified solid supports, including, but not limited to, metal binding moieties or surface-active amino acids. Depending on the technique used to separate his-tagged target polypeptides, unbound his-tagged polypeptide may appear in the flow-through. The unbound his-tagged polypeptide may be further purified using a metal-modified solid support.

The following non-limiting Examples are intended to be purely illustrative.

EXAMPLES

Example 1

Preparation Of Metal-Modified 3-[[[Bis(carboxymethyl)amino]acetyl]-amino]propyl Silica Magnetic Particles.

a) Preparation of 3-Aminopropyl-Modified Magnetic Silica Particles.

3-Aminopropyl-modified magnetic silica particles were prepared as follows. A 50-ml aliquot of 3-aminopropyltrimethoxysilane was added to a stirred solution of methanol (900 mL) followed by addition of water (50 mL). The mixture was added to 100 g of magnetic silica particles (MP-50, W. R. Grace, Columbia, Md.). The particles were kept in suspension for 4 hr at room temperature using intermittent agitation. The residual methanol/silane/water solution was removed and the support particles were washed with 3×1.2 L of water then resuspended in 1 L of methanol. The 3-aminopropyl-modified magnetic silica particles were collected by filtration and dried under vacuum. Elemental analysis confirmed the composition of the 3-aminopropyl-modified magnetic silica particles: C, 0.75; H, 0.64; N, 0.30.

b) Preparation of 3-[[[Bis(carboxymethyl)amino]acetyl]amino]-propyl Magnetic Silica Particles.

3-[[[Bis(carboxymethyl)amino]acetyl]amino]-propyl magnetic silica particles were made by first suspending 3-aminopropyl-modified magnetic silica particles (100 g), prepared as described above, in N,N-dimethylacetamide (600 mL), adding triethylamine (31 ml, 210 mmoles), and mixing thoroughly. 200 mmoles of 2,6-diketo-N-carboxymethyl-morpholine (prepared according to U.S. Pat. No. 3,621,018) in 400 ml of N,N-dimethylacetamide was added and the resulting mixture was kept in suspension for 4 hr at room temperature. The unreacted N,N-dimethylacetamide/anhydride/triethylamine solution was removed and the particles were washed with 3×1.2 L of water. Elemental analysis confirmed the composition of 3-[[[bis(carboxymethyl)amino]acetyl] amino]-propyl-modified magnetic silica particles: C, 1.06; H, 0.61; N. 0.17.

c) Preparation of Nickel (II) 3-[[[Bis(carboxymethyl)amino]-acetyl]amino]propyl Magnetic Silica Particles.

Nickel (II) 3-[[[bis(carboxymethyl)amino]-acetyl]amino]-propyl magnetic silica particles were prepared by suspending 100 grams of 3-[[[bis(carboxymethyl)amino]-acetyl]amino]-propyl magnetic silica particles, prepared as described above, in a 250 mM nickel (II) chloride solution (1 L) for 4 hours at room temperature. The excess nickel solution was removed and the resulting solid support was washed with five times with water.

Modified particles similar to those described above in Example 1(a)-(c) were prepared using starting particles other than magnetic silica particles from W. R. Grace. Other silica gels that have been used in steps (a)-(c) were supplied by: Sigma-Aldrich Corp (St. Louis, Mo.) (23,681-0, 23,682-9, and 23,684-5); Silicyle Inc. (Quebec, Calif.) (S10030M, 10040M, 100300T, S10040T, and R10030M); or J. T. Baker (Philipsburg, N.J.) (7314-02 and 7315-20). The commercial silica gels contained particles having diameters in the range of about 5 to about 500 microns, and pore sizes in the range of about 40 to about 1000 Angstroms.

d) Preparation of Colbalt (II) 3-[[[Bis(carboxymethyl)amino]-acetyl]amino]propyl Magnetic Silica Particles.

Cobalt (II) 3-[[[bis(carboxymethyl)amino]-acetyl]amino]-propyl magnetic silica particles were prepared by suspending 100 mg of a 3-[[[bis(carboxymethyl)amino]-acetyl]amino]-propyl magnetic silica particles, prepared as described above, in a 250 mM cobalt (II) chloride solution for two minutes at room temperature. The excess cobalt solution was removed and the resulting magnetic silica particles were washed 5 times with water.

e) Preparation of Copper (II) 3-[[[Bis(carboxymethyl)amino]-acetyl]amino]propyl Magnetic Silica Particles.

Copper (II) 3-[[[bis(carboxymethyl)amino]-acetyl]amino]-propyl magnetic silica particles were prepared by suspending 100 mg of a 3-[[[bis(carboxymethyl)amino]-acetyl]amino]-propyl magnetic silica particles, prepared as described above, in a $CuCl_2$ (250 mM) solution for two minutes at room temperature. The copper solution was removed and the resulting magnetic silica particles were washed three times with water.

f) Preparation of Zinc (II) 3-[[[Bis(carboxymethyl)amino]-acetyl]amino]propyl Magnetic Silica Particles.

Zinc (II) 3-[[[bis(carboxymethyl)amino]-acetyl]amino]-propyl magnetic silica particles were prepared by suspending 100 mg of a 3-[[[bis(carboxymethyl)amino]-acetyl]amino]-propyl magnetic silica particles, prepared as described above, in a $ZnCl_2$ (250 mM) solution for two minutes at room temperature. The zinc solution was removed and the resulting magnetic silica particles were washed three times with water.

Example 2

Preparation of Metal-Modified 3-[[[Bis(carboxymethyl)amino]acetyl]-amino]propyl Silica Gel.

(a) Preparation of 3-Aminopropyl-Modified Silica Gel.

3-Aminopropyltrimethoxysilane (125 mL) was added to a stirred solution of methanol (2000 mL) followed by addition of water (125 mL). This mixture was added to 250 g of silica gel (S10040T, 1000 angstom, Silicyle, Inc, Quebec, Canada) and the resulting mixture was kept in suspension for 4 hr at room temperature. After allowing the resin to settle the residual methanol/silane/water solution was decanted, the particles were washed with water (3×2.5 L) and resuspended in 2 L of methanol. The aminosilane-modified solid support was collected by filtration and dried under vacuum. Elemental analysis confirmed the composition of aminopropyl-modified solid support: C, 0.46; H, 0.30; N, 0.19.

(b) Preparation of 3-[[[Bis(carboxymethyl)amino]acetyl]amino]-propyl Silica Gel.

3-Aminopropyl-modified solid support (100 g) prepared as described above was suspended in N,N-dimethylacetamide (100 mL) and triethylamine (31 mL, 210 mmoles) was added to the mixture. This suspension was mixed thoroughly then 200 mmoles of 2,6-diketo-N-carboxymethylmorpholine (prepared according to U.S. Pat. No. 3,621,018, the contents of which are incorporated herein in its entirety) in 400 mL of N,N-dimethylacetamide was added and the resulting mixture was kept in suspension for 4 hr at room temperature. The unreacted N,N-dimethylacetamide/anhydride/triethylamine solution was removed and the solid support was washed with 4×1.2 L of water. Elemental analysis confirmed the composition of 3-[[[bis(carboxymethyl)amino] acetyl]amino]propyl solid support: C, 0.94; H, 0.32; N. 0.28.

(c) Preparation of Nickel (II) 3-[[[Bis(carboxymethyl)amino] acetyl]-amino]propyl Silica Gel.

A portion of 3-[[[bis(carboxymethyl)amino]acetyl]amino]propyl solid support prepared as described above was suspended in 250 mM nickel (II) chloride solution for 4 hr at room temperature. The excess nickel solution was removed and the resulting solid support was washed 5 times with water.

Example 3

Preparation of Propylethylenediamine-Modified Magnetic Silica Particles.

N-[3-(Trimethoxysilyl)propyl]ethylenediamine (2 mL) was added to a stirred solution of magnetic silica particles (2 g) in 95% methanol (8 mL). The resulting mixture was kept in suspension for 4 hr at room temperature. The residual methanol/silica solution was removed and the particles were washed with methanol (5×40 mL) and dried under vacuum. Elemental analysis confirmed the composition of aminopropylethylenediamine-modified silica magnetic solid support: C, 0.97; H, 0.70; N, 0.45.

Example 4

Preparation of Propylethylenediamine-Modified Silica Gel.

N-[3-(Trimethoxysilyl)propyl]ethylenediamine (2 mL) was added to a stirred solution of silica particles (1.0 g of Davisil, grade 644 silica gel, 100-200 mesh, 150 A pore size) in 95% methanol (8 mL). The resulting mixture was kept in suspension for 4 hr at room temperature. The residual methanol/silica solution was removed and the particles were washed with methanol, 5×40 mL, and dried under vacuum. Elemental analysis confirmed the composition of aminopropylethylenediamine-modified silica solid support: C, 5.82; H, 1.49; N, 2.44.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

Example 5

Removal of hemoglobin and fractionation of target proteins using 3-aminopropyl-modified magnetic silica particles.

The ability of 3-aminopropyl modified magnetic silica particles to fractionate proteins and to remove hemoglobin from rabbit reticulocyte lysate spiked with β-galactosidase and calf intestinal alkaline phosphatase was evaluated in parallel with Q-sepharose (BioRad, Foster City, Calif.) and DEAE sepharose (Sigma-Aldrich, Milwaukee, Wis.). A sample containing untreated rabbit reticulocyte lysate (100 μl), 1 ml 20 mM Tris-buffer (pH 8.3), 8 μl stock β-galactosidase (Promega Corp.), 40 μl calf intestinal alkaline phosphatase (Promega Corp.) was prepared. Aliquots (400 μl) of the sample were to applied to pre-equilibrated 3-aminopropyl-modified magnetic silica particles (40 mg), prepared as described above, in 1.5 ml Eppendorf tubes, and mixed at room temperature. The particles were separated from the supernatant (or flow through) by placing the tubes on a magnetic stand, and the supernatant was removed and reserved. The particles were washed twice with 400 μl 200 mM Tris buffer (pH 8.3). Bound proteins (β-galactosidase and calf intestinal alkaline phosphatase) were eluted with a sequential application of 20 mM Pipes buffer (pH 6.7), 20 mM sodium citrate (pH 5.0), followed by two applications of 1 M ammonium acetate in 20 mM Tris-buffer (pH 8.3). The separation procedure as described above for the 3-aminopropyl-modified magnetic silica particles was used to evaluate hemoglobin removal and protein fractionation on Q-sepharose or DEAE sepharose.

The hemoglobin content of each supernatant was measured by diluting an aliquot of the supernatant 1:20 with water and measuring the absorbance at 415 nm.

β-galactosidase activity was measured as follows. Promega 2× Assay Buffer [E203A, 14041201] was diluted 1:1 with nanopure water, and 490 μl buffer was added to 1.5 ml plastic microfuge tubes. Ten microliters of test fractions was added to the tubes. As a control, 10 microliters of 20 mM Tris buffer pH 8.3 was added in place of the test fraction. The tubes were incubated at RT for 45 min. A 0.5 ml aliquot of sodium carbonate solution [Promega E202A, 14679601] was added to each tube, and the absorbances of the solutions were read at 420 nm, using the control tube as a blank.

Phosphatase activity was measured as follows. A phosphatase assay reagent of a saturated solution of p-nitrophenyl phosphate was prepared by mixing 48 ml of 100 mM Tris buffer pH 8.3 with p-nitrophenyl phosphate solution, which was made by suspending solid p-NPP (Sigma Chemical Co.) in 100% ethanol in an amount that would generate a 20 mM solution if all the material would dissolve. Nine hundred microliters of the saturated solution was placed in 1.5 ml microfuge tubes and 2 μl of the fractions added to the tubes. As a control, 2 μl of 20 mM Tris pH 8.3 was added in place of the test fractions. The tubes were incubated 120 min at 37° C., and the absorbance at 420 nm was measured after blanking the spectrophotometer with the control solution.

The results are presented graphically in FIG. 1A (aminopropyl-modified magnetic silica particles), FIG. 1B (Q-sepharose), and FIG. 1C (DEAE sepharose). When aminopropyl-modified magnetic silica particles were used to fractionate proteins in the starting material, most of the hemoglobin was found in the unbound flow through fraction (FIG. 1A). In contrast, with both Q-sepharose and DEAE sepharose, the largest percentage of hemoglobin bound to the resin and was eluted by the 20 mM Pipes buffer (pH 6.7), and a substantial amount of hemoglobin eluted by 20 mM sodium citrate (pH 5.0). Fractionation of β-galactosidase and calf intestinal alkaline phosphatase was achieved by eluting bound protein from aminopropyl-modified magnetic silica particles using different elution buffers (FIG. 1A).

Example 6

Separation of FluoroTect-labeled luciferase from hemoglobin using 3-aminopropyl silica magnetic particles 3-aminopropyl-modified magnetic silica particles were used to fractionate proteins from rabbit reticulocyte lysate. FluoroTect Green in vitro translation labeling system (Promega Corp., Madison, Wis.) was used to express FluoroTect-labeled luciferase in rabbit reticulocyte lysate according to the manufacturer's instructions. Following translation, 20 µl of the translation reaction mixture was mixed with 5 mg aminopropyl-modified silica magnetic particles (100 mg/ml) pre-equilibrated in 20 mM MOPS buffer (pH 6.8) in 1.5 ml Eppendorf tubes. The particles were resuspended by mixing at room temperature. The particles were separated from the supernatant by placing the tubes on a magnetic stand and removing the supernatant, which was reserved for subsequent analysis. The particles were washed twice with 1 ml 20 mM MOPS buffer (pH 6.8). The particles were treated with either 2 M ammonium acetate (pH 6.5) or 1 M NaCl, and the purification fractions were collected and analyzed by SDS-PAGE (FIG. 2). With reference to FIG. 2, the gel was loaded as follows: Lane M, protein molecular weight marker (Promega Corp.); lanes 1 and 2, control containing 10 µl of reaction mixture+40 µl of buffer; lanes 4 and 5, ammonium acetate (pH 6.5) eluate; lanes 6-9, 1 M NaCl eluate.

As can be seen by comparing lanes 1 and 2 with lanes 4 and 5 of the gel shown in FIG. 2, luciferase was recovered in the fraction eluted with ammonium acetate (pH 6.5), with a significant reduction in hemoglobin, indicating that a substantial amount of hemoglobin appeared in the flow through fraction and did not bind to the particles.

Example 7

Capturing membrane vesicles used in in vitro translation using 3-aminopropyl magnetic silica particles In vitro protein synthesis: Core glycosylation control mRNA (S. cerevisiae alpha factor) was translated using rabbit reticulocyte lysate (Promega Corp. Madison, Wis.) for 60 min at 30° C. Reaction mixtures (25 µl), prepared as summarized in Table 1, contained 17.5 µl of reticulocyte lysate, 0.5 µl of RNasin (40 units/µl), 0.5 µl of 1 mM amino acids (minus methionine), 20 µCi of L—[$^{35}$S] methionine (Amersham), 2 µl of 0.1 µg/µl core glycosylation control RNA, and, optionally, either canine microsomal membrane (Promega Corp.) or HeLa microsomal membrane vesicles (prepared at Promega Corp.) from HeLa cell line (HeLa-S3) (Biovest International Inc., Englewood Cliffs, N.J.). Reactions were analyzed by SDS-PAGE on a 4-20% Novex gel, transferred to a sheet of PVDF, and exposed to a PhosphoImager cassette for 16 hr.

TABLE 1

|  | 1 | 2 | 3 | 4 | 5 | 6 | 7 | 8 | 9 | 10 |
|---|---|---|---|---|---|---|---|---|---|---|
| Rabbit RetiLysate | 17.5 | 17.5 | 17.5 | 17.5 | 17.5 | 17.5 | 17.5 | 17.5 | 17.5 | 17.5 |
| Water | 2.5 | 1.5 | 1.5 | 3.5 | 3.5 | 3.5 | 2.5 | 2.5 | 3.5 | 3.5 |
| Rnasin | 0.5 | 0.5 | 0.5 | 0.5 | 0.5 | 0.5 | 0.5 | 0.5 | 0.5 | 0.5 |
| Amino Acid (-Met) | 0.5 | 0.5 | 0.5 | 0.5 | 0.5 | 0.5 | 0.5 | 0.5 | 0.5 | 0.5 |
| RNA template* | – | 1.0 | 1.0 | 1.0 | 1.0 | – | 1.0 | 1.0 | 1.0 | 1.0 |
| 35 S Met | 2.0 | 2.0 | 2.0 | 2.0 | 2.0 | 2.0 | 2.0 | 2.0 | 2.0 | 2.0 |
| CMM** | 2.0 | 2.0 | 2.0 | – | – |  |  |  |  |  |
| HMM*** |  |  |  |  |  | 1.0 | 1.0 | 1.0 | – | – |
| Particles | + | + | – | + | – | + | + | – | + | – |

Figure 3A:
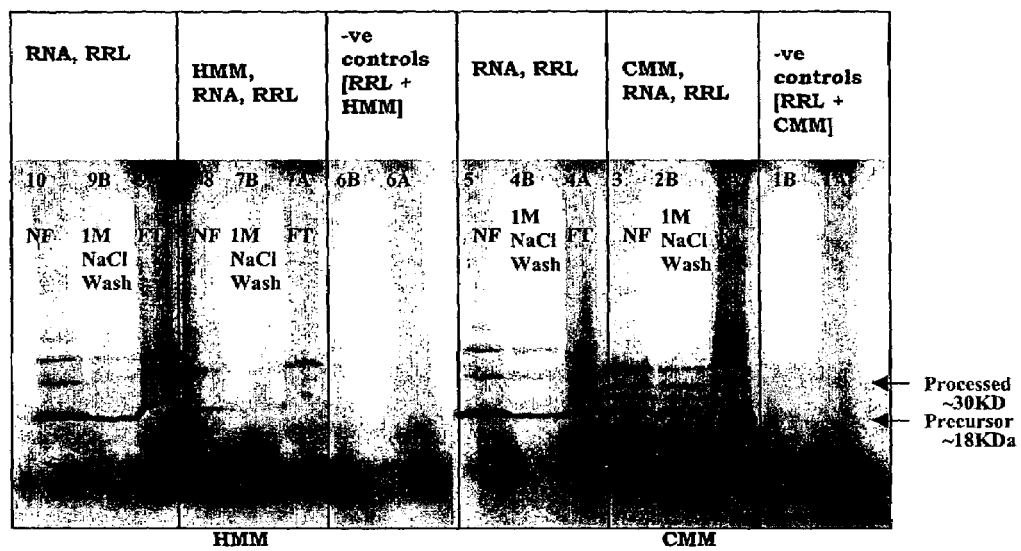
FIG. 3A and 3B are SDS-PAGE gels of glycosylated membrane proteins captured by 3-aminopropyl magnetic silica particles.
Figure 3B:
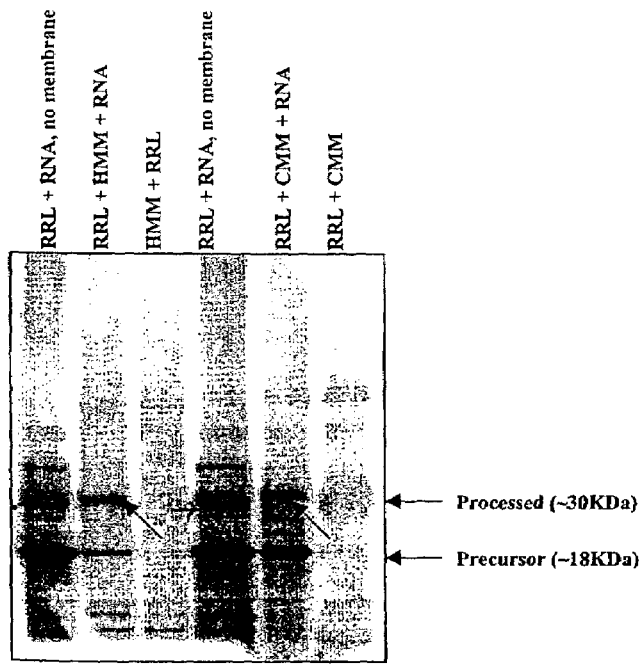

*Glycosylation control mRNA (S. cerevisiae α-factor)
**Canine Microsomal membrane
***HeLa Microsomal membrane Aliquots of 3-aminopropyl magnetic silica particles (60 mg/ml) were added to 25 µl of the translation reaction mixture, as indicated in Table 1. SDS buffer 4×(10 µl) was added to ~20-25 µl of the supernatant (flow through), heat denatured and examined by SDS-PAGE. The particles were washed once with 1 ml 20 mM MOPS buffer (pH 6.8) and proteins eluted with 25 µl of 1 M NaCl in MOPS buffer (pH 6.8). The eluate was mixed with 10 µl of 4×SDS buffer, heat denatured, and examined by SDS-PAGE. 10 µl of 1 M NaCl in MOPS buffer (pH 6.8) and 10 µl of 4×SDS buffer were added to the aminopropyl magnetic silica particles, heat denatured and examined by SDS-PAGE. As a control, aliquots (3 µl) of reaction mixtures not contacted with aminopropyl magnetic silica particles were treated with 20 µl of 20 mM MOPS (pH 6.8) and 10 µl of 4×SDS buffer, heat denatured and examined by SDS-PAGE. (FIG. 3). The results of this experiment demonstrate that proteins expressed in vitro and modified post-translationally can be separated and analyzed using 3-aminopropyl magnetic silica particles.

Example 8

Identifying and purifying membrane proteins.

Figure 4:
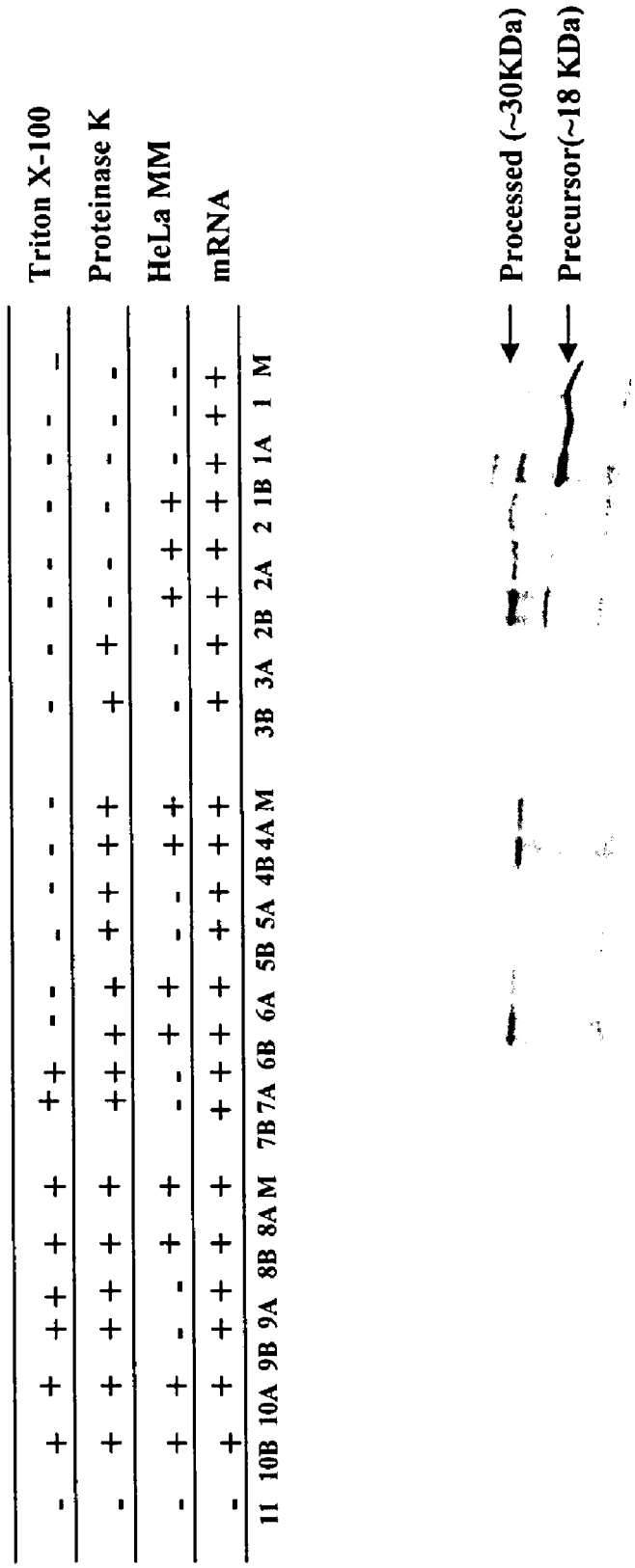
FIG. 4 is an SDS-PAGE gel of membrane proteins expressed in cell-free expression systems isolated using 3-aminopropyl magnetic silica particles.

S. cerevisiae □-factor mRNA was translated using rabbit reticulocyte lysate (Promega corporation, Madison, Wis.) in a 50 μl reaction for 60 minutes in the presence of HeLa microsomal membrane vesicles prepared at Promega Corporation from HeLa cell line (HeLa-S3) (Biovest International Inc.). The translation reaction (50 μl each) contained 35.0 μl of reticulocyte lysate, 1.0 μl of RNasin (40units/μl), 1.0 μl of 1 mM amino acids (minus methionine), 20 μCi of L—[$^{35}$S] methionine [Amersham Biosciences, Sunnyvale, Calif.], 2 μl of 0.1 μg/μl core glycosylation control RNA, and HeLa microsomal membrane vesicles. A portion of the reaction mixture was treated with 4×SDS buffer, heat denatured, and analyzed by SDS-PAGE on a 4-20% Novex gel. The gel was transferred onto a sheet of PVDF and exposed to a PhosphorImager cassette for 16 hr for analysis (FIG. 4).

Below is a summary of the alternative treatments the various reaction mixtures were subjected to prior to separation by SDS-PAGE.

(1) After the translation reaction, the reaction mixture was added to the 3-aminopropyl magnetic silica particles either in a 1:1 ratio (i.e., 10 μl of mixture to 10 μl of particles) or in a 1:~1.7 ratio (i.e., 30 μl of mixture to 50 μl of particles). The particle mixture was washed 1× with 1 ml of 20 mM MOPS buffer. The particles were treated with 20 μl of 1 N NaCl in 20 mM MOPS buffer and 10 μl of 4×SDS buffer. The particle mixture was heat denatured and the supernatant was analyzed by SDS-PAGE, as shown in FIG. 4, lanes 1A, 1B and 2A, 2B.

(2) After the translation reaction, 3-aminopropyl magnetic silica particle capture was followed by limited proteolysis using proteinase K. The reaction mixture was added to the 3-aminopropyl magnetic silica particles either in a 1:1 ratio (i.e., 10 μl of mixture to 10 μl of particles) or in a 1:~1.2 ratio (i.e., 40 μl of mixture to 50 μl of particles). The particles were washed 1× with 1 ml of 20 mM MOPS buffer and treated with 10 μl of 50 mM Tris/CaCl$_2$ buffer and 2 μl of 50 mM CaCl$_2$. The mixture was incubated on ice for 10 min. Following incubation, proteinase K (1 μl of 1 mg/ml) or, alternatively, proteinase K (1 μl of 1 mg/ml) and Triton X-100 (1 μl of 10%) was added and the resulting mixture was incubated on ice for 1 hr. The proteinase K reaction was stopped by adding 2 μl of 2 mg/ml PMSF. Also added was 5 μl of 20 mM MOPS buffer and 10 μl of 4×SDS. The reaction mixture was heat denatured and analyzed by SDS-PAGE. When 40 μl of mixture was used in the reaction, the following reagents were also increased by 4-fold: Tris/CaCl$_2$ buffer, 50 mM CaCl$_2$, 1 mg/mL Proteinase K, Triton X-100 (1 μl of 10%), PMSF 2 mg/mL. A small amount of reaction mixture was used for gel analysis. Then, to the reaction particles was added 10 μl of 4×SDS buffer. The particle mixture was heat denatured and the supernatant was analyzed by SDS-PAGE, as shown in FIG. 4 lanes 3A, 3B and 4A, 4B or as shown in FIG. 4 lanes 7A, 7B and 8A, 8B using Triton X-100 to solubilize membrane proteins.

(3) After the translation reaction, proteinase K treatment followed by 3-aminopropyl magnetic silica particle capture of the membrane vesicles were performed. The reaction mixture (i.e., 10 μl) was added to 2 μl of 50 mM CaCl$_2$. The mixture was incubated on ice for 10 min. Proteinase K (1 μl of 10 mg/ml) or Proteinase K (1 μl of 1 mg/ml) and Triton X-100 (1 μl of 10%) was added to the reaction mixture and allowed to incubate for 1 hr on ice. The reaction was stopped by adding 2 μl of 2 mg/ml PMSF. The 3-aminopropyl magnetic silica particles (10 μl) were added to the mixture. The particle suspension was allowed to settle and the particles were washed 1× with 1 ml of 20 mM MOPS. To elute the membrane bound proteins, 20 μl of 1 N NaCl in 20 mM MOPS buffer was added to the particles. In preparation for SDS-PAGE analysis, 10 μl of 4×SDS buffer was added to the mixture. The mixture was subsequently heat-denatured and analyzed by SDS-PAGE. When 40 μl of mixture was used in the reaction, the following reagents were also increased by 4× the volume: Tris/CaCl$_2$ buffer, 50 mM CaCl$_2$, 1 mg/mL Proteinase K, Triton X-100 (1 μl of 10%), PMSF 2 mg/mL. A small amount of reaction mixture was used for gel analysis. The reaction particles were combined with 10 μl of 4×SDS buffer, the particle mixture was heat denatured, and the supernatant was analyzed by SDS-PAGE, as shown in FIG. 4 lanes 5A, 5B and 6A, 6B or as shown in FIG. 4 lanes 9A, 9B and 10A, 10B, using Triton X-100 to solubilize membrane proteins.

The gel shown in FIG. 4 was loaded as follows:

Lane M; Marker

Lane 1: RRL+mRNA

Lane 1A: RRL+mRNA—3-aminopropyl magnetic silica particle capture (10 μl of reaction mixture+10 μl of 3-aminopropyl magnetic silica particles)

Lane 1B: RRL+mRNA—3-aminopropyl magnetic silica particle capture (30 μl of reaction mixture+50 μl of 3-aminopropyl magnetic silica particles)

Lane 2: RRL+mRNA+HMM

Lane 2A: RRL+mRNA+HMM—3-aminopropyl magnetic silica particle capture (10 μl of reaction mixture+10 μl of 3-aminopropyl magnetic silica particles)

Lane 2B: RRL+mRNA+HMM—3-aminopropyl magnetic silica particle capture (30 μl of reaction mixture+50 μl of 3-aminopropyl magnetic silica particles)

Lane 3A: RRL+mRNA—3-aminopropyl magnetic silica particle capture—Proteinase K treatment (10 μl of reaction mixture+10 μl of 3-aminopropyl magnetic silica particles)

Lane 3B: RRL+mRNA—3-aminopropyl magnetic silica capture—Proteinase K treatment (40 μl of reaction mixture+50 μl of 3-aminopropyl magnetic silica particles)

Lane 4A: RRL+mRNA+HMM—3-aminopropyl magnetic particle capture—Proteinase K treatment (10 μl of reaction mixture+10 μl of 3-aminopropyl magnetic silica particles)

Lane 4B: RRL+mRNA+HMM—3-aminopropyl magnetic silica particles capture—Proteinase K treatment (40 μl of reaction mixture+50 μl of 3-aminopropyl magnetic silica particles)

Lane 5A: RRL+mRNA—Proteinase K treatment—3-aminopropyl magnetic silica particle capture (10 μl of reaction mixture+10 μl of amino-silica magnetic particles)

Lane 5B: RRL+mRNA—Proteinase K treatment—3-aminopropyl magnetic silica particle capture (40 μl of reaction mixture+50 μl of 3-aminopropyl magnetic silica particles)

Lane 6A: RRL+mRNA+HMM—Proteinase K treatment—3-aminopropyl magnetic silica particle capture (10 μl of reaction mixture+10 μl of 3-aminopropyl magnetic silica particles)

Lane 6B: RRL+mRNA+HMM—Proteinase K treatment—3-aminopropyl magnetic silica particle capture (40 μl of reaction mixture+50 μl of 3-aminopropyl magnetic silica particles)

Lane 7A: RRL+mRNA—3-aminopropyl magnetic silica particle capture—Proteinase K treatment+Triton X-100 (10 μl of reaction mixture+10 μl of 3-aminopropyl magnetic silica particles)

Lane 7B: RRL+mRNA—3-aminopropyl magnetic silica particle capture—Proteinase K treatment+Triton X-100 (40 μl of reaction mixture+50 μl of 3-aminopropyl magnetic silica particles)

Lane 8A: RRL+mRNA+HMM—3-aminopropyl magnetic silica particle capture—Proteinase K treatment+Triton X-100 (10 μl of reaction mixture+10 μl of 3-aminopropyl magnetic silica particles)

Lane 8B: RRL+mRNA+HMM—3-aminopropyl magnetic silica particle capture—Proteinase K treatment+Triton X-100 (40 μl of reaction mixture+50 μl of 3-aminopropyl magnetic silica particles)

Lane 9A: RRL+MRNA—Proteinase K treatment+Triton X-100 —3-aminopropyl magnetic silica particle capture (10 μl of reaction mixture+10 μl of 3-aminopropyl magnetic silica particles)

Lane 9B: RRL+MRNA—Proteinase K treatment+Triton X-100 —3-aminopropyl magnetic silica particle capture (40 μl of reaction mixture+50 μl of 3-aminopropyl magnetic silica particles)

Lane 10A: RRL+mRNA+HMM—Proteinase K treatment+Triton X-100 —3-aminopropyl magnetic silica particle capture (10 μl of reaction mixture+10 μl of 3-aminopropyl magnetic silica particles)

Lane 10B: RRL+mRNA+HMM—Proteinase K treatment+Triton X-100 —3-aminopropyl magnetic silica particle capture (40 μl of reaction mixture+50 μl of 3-aminopropyl magnetic silica particles)

Lane 11: RRL

RRL: Rabbit reticulocyte lysate

HMM: HeLa microsomal membrane preparation

The results of this experiment demonstrate that membrane proteins expressed in cell free protein expression systems can be rapidly identified and characterized using 3-aminopropyl magnetic silica particles.

Example 9

Capture of bacterial cells by 3-aminopropyl magnetic silica particles

Figure 5:
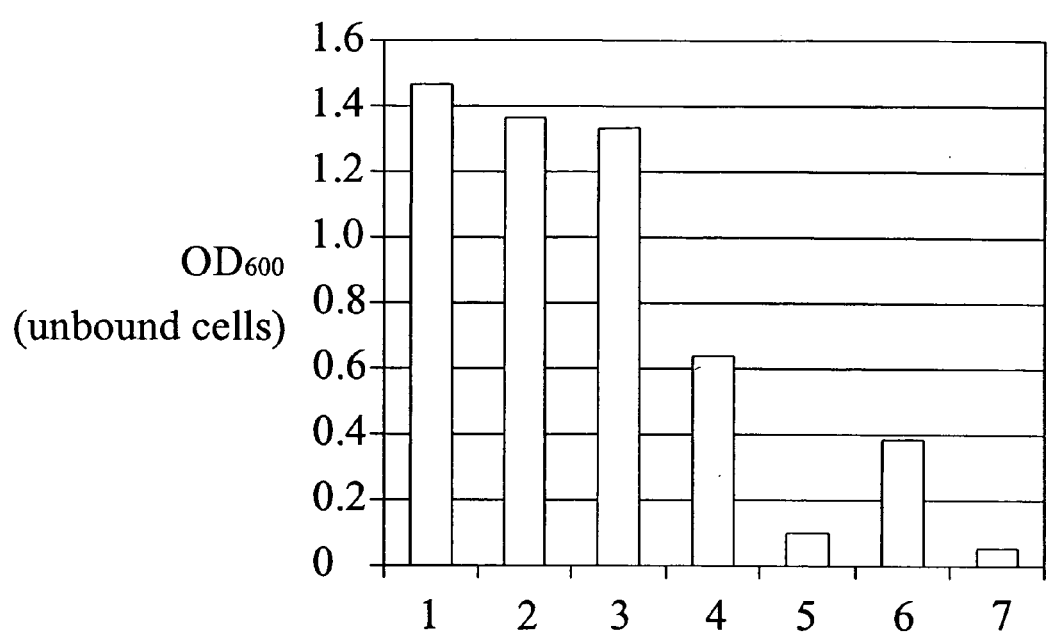
FIG. 5 is a graph illustrating capture of bacterial cells by 3-aminopropyl-modified magnetic silica particles.

Bacterial cells (*E. coli* JM109) were cultured overnight at 37° C. in Luria broth. Culture suspensions (500 μl each) were transferred to separate Eppendorff tubes. Samples treated with 15% isopropanol were prepared by adding 150 μl of 100% isopropanol and 350 μl of sterile double distilled water to the tubes. Samples treated with 30% isopropanol were prepared by mixing 300 μl of 100% isopropanol and 200 μl of sterile double distilled water with the cells. Samples treated with 15% isopropanol and 1 M NaCl were prepared by mixing 150 μl of 100% isopropanol, 200 μl of 5 M NaCl and 150 μl of sterile double distilled water with the cells. Samples treated with 30% isopropanol and 1 M NaCl were prepared by mixing 300 μl of 100% isopropanol and 200 μl of 5 M NaCl with the cells. 3-aminopropyl magnetic silica particles (10 mg) were added to each tube and mixed with for 1 minute. No particles were added to the control. Unbound cells in the supernatant were removed by placing the tubes onto a magnet to capture the magnetic silica particles and $OD_{600}$ of the supernatant was measured. The results are summarized in FIG. 5, which shows the $OD_{600}$ of unbound cells from: (1) the control containing no particles; (2) culture treated with double distilled water; (3) culture treated with 1 M NaCl; (4) culture treated with 15% isopropanol; (5) culture treated with 30% isopropanol; (6) culture treated with 15% isopropanol and 1M NaCl; and (7) culture treated with 30% isopropanol and 1M NaCl.

The 3-aminopropyl magnetic silica particles were able to bind bacterial cells directly from a culture in one minute or less. The number of cells bound by the particles was enhanced by the addition of isopropanol and sodium chloride. The $OD_{600}$ of the supernatant of cultures treated with 15 or 30% isopropanol was considerably lower than that of untreated cells, which indicates that 3-aminopropyl magnetic silica particles are effective in binding cells treated with isopropanol.

Example 10

Separation of polypeptides using nickel (II) 3-[[[Bis(carboxymethyl)amino]-acetyl]amino]-propyl magnetic silica particles Preparation of Cell Lysate Bacterial cells (*E. coli* JM109) expressing his-tagged proteins were grown overnight in 50 ml LB medium containing tetracylcine at 37° C. These cells diluted 1:100 in a fresh LB medium containing tetracylcine and were grown at 37° C. until the OD 600 was between 0.4-0.6. IPTG was added to a final concentration of 1 mM the cells were induced for at least 3 hours. The cells were pelleted by centrifugation and resuspended in 100 μl binding buffer containing 100 mM Hepes (pH 7.5) and 10 mM imidazole. Cells were broken by sonication and centrifuged to remove unbroken cells and cell debris. The supernatant was used subsequent for purification experiments described below. In some cases, rather than using sonication to disrupt the cells, cells were disrupted by lysis with various detergents commonly used to lyse bacterial cells. The use of the detergents did not interfere with isolation of proteins.

Purification of Polypeptides Under Non-denaturing Conditions

Nickel (II) 3-[[[Bis(carboxymethyl)amino]-acetyl]amino]-propyl magnetic silica particles (3 mg), prepared as described above, were combined with sonicated cells containing his-tag protein and mixed by pipetting or by shaking for approximately 1-5 minutes. The tubes were placed on a magnetic stand to separate the particles from the supernatant, and the supernatant was removed. The particles were washed three times with 150 μl binding buffer. His-tag proteins bound to the particles were eluted with elution buffer (100 mM Hepes pH 7.5 and 0.1 to 0.5 M imidazole). Protein concentrations were measured using Pierce protein assay system, and the protein was analyzed by SDS-PAGE (FIG. 6).

Figure 6:
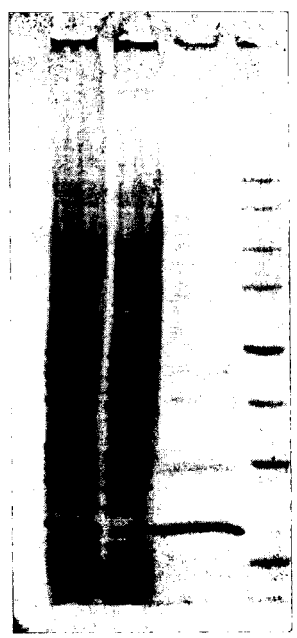
FIG. 6 is an SDS-PAGE gel of his-tagged RNase HI purified using nickel (II) 3-[[[bis(carboxymethyl)amino]-acetyl]amino]-propyl magnetic silica particles.

FIG. 6 shows the separation using the particles of his-RNaseHI from other proteins in the cell lysate. Lane 1, lysate not contacted with the particles; lane 2 flow through of lysate contacted with particles; lane 3, proteins eluted from particles with 0.5 M imidazole; and lane 4, size marker.

Purification of Polypeptide Under Denaturing Conditions

Before sonication or cell lysis using lysis buffer, urea or guanidine-HCl was added to cells to give a final concentration of 6 M. 30 μl of nickel (II) 3-[[[Bis(carboxymethyl)amino]-acetyl]amino]-propyl magnetic silica particles was added to the cell lysate. The particles were mixed by pipetting or by shaking for approximately 1-5 minutes. The particles and supernatant were separated by placing the tubes on a magnetic stand and the supernatant was removed. The particles were washed three times (150 μl each) with binding buffer containing 6 M urea or guanidine-HCl. His-tag proteins bound to the particles were eluted with elution buffer (100 mM Hepes pH 7.5, 0.1-0.5 M imidazole and 6 M urea or guanidine-HCl). The purified protein was analyzed by SDS-PAGE or functional assay. Protein concentrations were measured using Pierce protein assay system. The presence of 6 M urea or guanidine-HCl did not interfere with binding or elution of his-tagged proteins (data not shown).

Example 11

Figure 7:
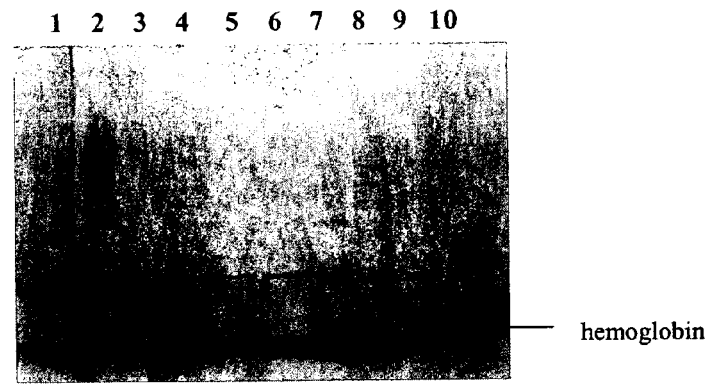
FIG. 7 is an SDS-PAGE gel comparing fractionation of hemoglobin using various metal 3-[[[bis(carboxymethyl)amino]-acetyl]amino]-propyl magnetic silica particles.

Purification and separation of hemoglobin using nickel/zinc/copper/cobalt (II) 3-[[[Bis(carboxymethyl)amino]-acetyl]amino]-propyl magnetic silica particles Nickel 3-[[[Bis(carboxymethyl)amino]-acetyl]amino]-propyl magnetic silica particles, copper (II) 3-[[[Bis(carboxymethyl)amino]-acetyl]amino]-propyl magnetic silica particles, cobalt 3-[[[Bis(carboxymethyl)amino]-acetyl]amino]-propyl magnetic silica particles, and zinc 3-[[[Bis(carboxymethyl)amino]-acetyl]amino]-propyl magnetic silica particles were prepared as described above. Rabbit reticulocyte lysate (Promega Corporation) (200 µl) was spiked with 25 µl of purified his-luciferase proteins. A 50 µl-aliquot of the lysate was added to each of four separate tubes containing 10 mg of nickel, copper, zinc, or cobalt 3-[[[Bis(carboxymethyl)amino]-acetyl]amino]-propyl magnetic silica particles. The particles were mixed with the lysate for 1-5 minutes by pipetting or shaking. The tubes were placed on a magnetic stand to separate the particles and supernatant, and the supernatant was removed. The particles were washed three times (150 µl each) with binding buffer containing 100 mM Hepes (pH 7.5). The proteins were eluted with 100 µl elution buffer (100 mM Hepes pH 7.5 and 0.1 or 0.5 M imidazole) and analyzed by SDS-PAGE (FIG. 7). The results indicate that hemoglobin binds to nickel, copper, zinc, or cobalt 3-[[[Bis(carboxymethyl)amino]-acetyl]amino]-propyl magnetic silica particles, and that these particles can be used to separate hemoglobin from proteins that do not bind to the particles.

Example 12

Separation of target from non-target polypeptides using Ni (II) 3-[[[Bis(carboxymethyl)amino]acetyl]amino]-propyl magnetic silica particles and 3-aminopropyl magnetic silica particles (a) Purification of Target Protein by Pre-treatment of the Target Containing Mixture with an Aminopropyl-modified Solid Support.

Figure 8:
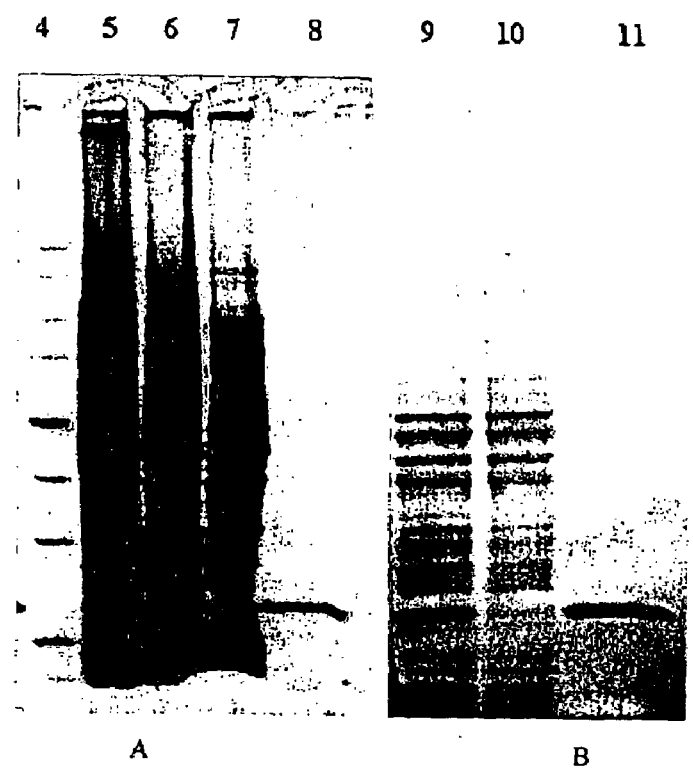
FIG. 8A is an SDS-PAGE gel of his-tagged RNase HI fractionated using aminopropyl-modified magnetic silica particles followed by nickel (II) 3-[[[bis(carboxymethyl)amino]-acetyl]amino]-propyl magnetic silica particles.

A cell lysate (100 µl) of *E. coli* JM109 expressing His-RNaseHI was prepared by sonicating the cells in a binding buffer containing 20 mM Tris (pH 7.5), 0.5 M NaCl, and 20 mM imidazole. The lysate was combined with 3-aminopropyl magnetic silica particles (50 mg), mixed by pipetting 10 times, and incubated for 2 minutes. The supernatant was separated from the 3-aminopropyl magnetic silica particles and mixed with 3 mg of Ni (II) 3-[[[Bis(carboxymethyl)amino]acetyl]amino]-propyl magnetic silica particles by pipetting (10×) for 2 minutes. The supernatant, which contained primarily non-target proteins, was removed and discarded. The Ni (II) 3-[[[Bis(carboxymethyl)amino]acetyl]amino]-propyl particles were washed 3 times with 150 µl of a buffer containing 20 mM Tris (pH 7.5), 0.5 M NaCl, and 20 mM imidazole. The His RNaseHI was then eluted with an elution buffer (100 µl) containing 20 mM Tris (pH 7.5), 0.5 M NaCl, and 0.5 M imidazole. The samples were analyzed by gel electrophoresis (FIG. 8). With reference to FIG. 8, lane 4 contains a marker, lane 5 contain the unfractionated bacterial lysate, lane 6 contains the flow-through solution from 3-aminopropyl magnetic particles, lane 7 contains the flow-through from Ni (II) 3-[[[Bis(carboxymethyl)amino]acetyl]amino]-propyl magnetic silica particles, lane 8 contains the 0.5 M imidazole eluate from the Ni (II) 3-[[[Bis(carboxymethyl)amino]acetyl]amino]-propyl magnetic silica particles, lane 9 contains the flow through fraction from 3-aminopropyl magnetic silica particles, lane 10 contains the flow through from Ni (II) 3-[[[Bis(carboxymethyl)amino]acetyl]amino]-propyl magnetic silica particles, and lane 11 contains the 0.5 M imidazole eluate from the Ni (II) 3-[[[Bis(carboxymethyl)amino]acetyl]amino]-propyl magnetic silica particles.

(b) Purification of Target Protein by Posttreatment of the Target-containing Mixture with an Aminopropyl-modified Solid Support.

A cell lysate of *E. coli* JM109 expressing his-tagged luciferase was prepared by sonicating JM109 cells in a binding solution containing 20 mM Tris (pH 7.5), 0.5 M NaCl, and 20 mM imidazole. The lysate (100 µl) was mixed with 3 mg of Ni (II) 3-[[[Bis(carboxymethyl)amino]acetyl]amino]-propyl magnetic silica particles by pipetting (10×) for 2 minutes. The particles were separating from the binding solution using a magnet and washed with three times with 150 µl of the binding solution. The target protein was eluted by adding 100 µl of 20 mM Tris (pH 7.5), 0.5M NaCl, and 0.5 M imidazole, pH 7.5. The eluted target protein was further purified from residual background polypeptides by mixing with 3 mg of 3-aminopropyl magnetic silica particles for 2 minutes and separating the target-containing supernatant from the particles. The samples were analyzed by gel electrophoresis (results not shown).

The results indicate that 3-aminopropyl magnetic silica particles, used in conjunction with Ni (II) 3-[[[Bis(carboxymethyl)amino]acetyl]amino]-propyl magnetic silica particles, facilitate removal of contaminating proteins Example 13

Figure 9A:
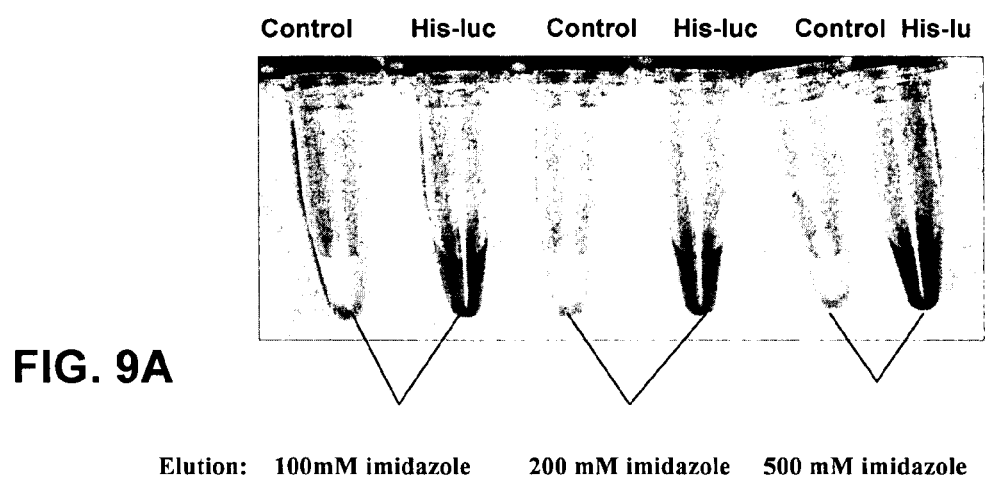
FIG. 9A is a photograph showing that Coomasie blue dye binds to his-tagged luciferase attached to nickel (II) 3-[[[bis(carboxymethyl)amino]-acetyl]amino]-propyl magnetic silica particles.
Figure 9B:
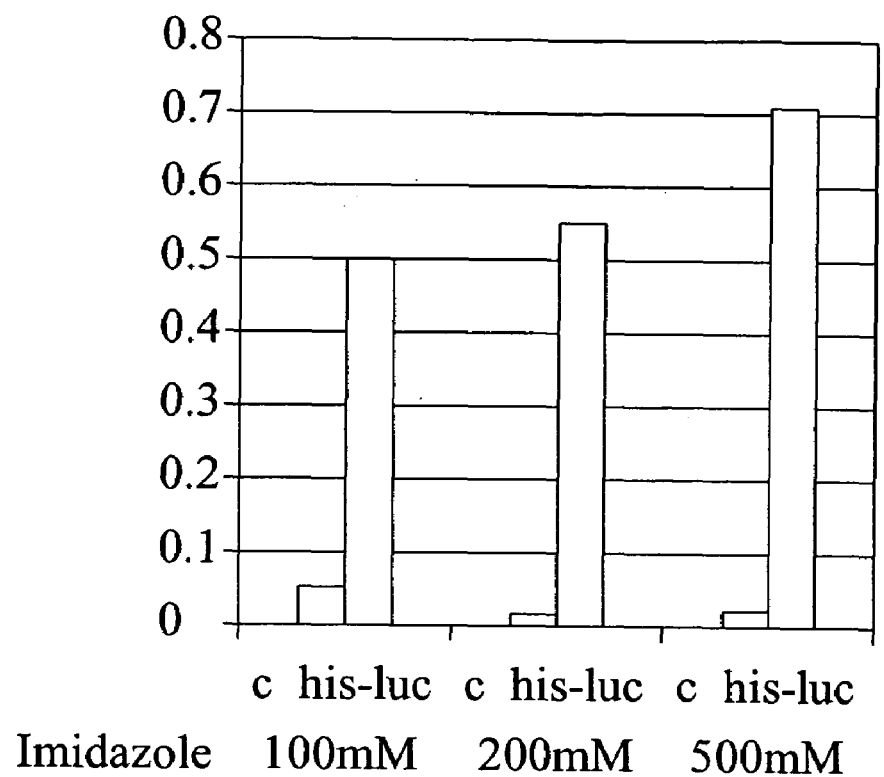
FIG. 9B is a photograph showing elution of Coomasie blue-stained his-tagged luciferase from nickel (II) 3-[[[bis(carboxymethyl)amino]-acetyl]amino]-propyl magnetic silica particles with increasing concentrations of imidazole.
Figure 9C:
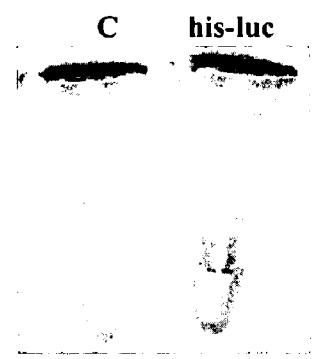
FIG. 9C is a photograph comparing the Coomasie blue dye binding to his-tagged proteins attached to nickel (II) 3-[[[bis(carboxymethyl)amino]-acetyl]amino]-propyl magnetic silica particles with that of other metal chelating resins.

Method for the Quantitation of Polypeptides Using Nickel (II) 3[[[Bis(carboxymethyl)amino]acetyl]amino]-propyl Magnetic Silica Particles Aliquots of lysate from bacteria expressing his-luciferase (100 µl) were placed into three Eppendorff tubes and mixed with 50 µl nickel (II) 3-[[[Bis(carboxymethyl)amino]acetyl]amino]-propyl magnetic silica particles, prepared as described above, by pipetting for 1-2 minutes. Particles to which no lysate was added were used as a control. The particles were washed with 1 ml of 100 mM Hepes (pH 7.5). An aliquot (100 µl) of 1% Coomassie blue in 100 mM Hepes (pH 7.5) was added to the washed particles and to the control particles. The particles were washed extensively with 100 mM Hepes pH 7.5 until the wash buffer was clear. The his-tagged luciferase was eluted with 0.1 M imidazole, 0.2 M imidazole, or 0.5 M imidazole and the collected eluate was photographed (FIG. 9A). The absorbance was measured by a spectrophotometer at a wavelength of 595 nm (FIG. 9B). The amount of labeled protein recovered was positively correlated with the concentration of imidazole used to elute the protein. In a parallel experiment, nickel agarose beads (Qiagen) were substituted for the µl nickel (II) 3-[[[Bis(carboxymethyl)amino]-acetyl]amino]-propyl magnetic silica particles, the labeled proteins eluted with 0.5 M imidazole, and the eluate photographed (FIG. 9C).

Figure 23B:
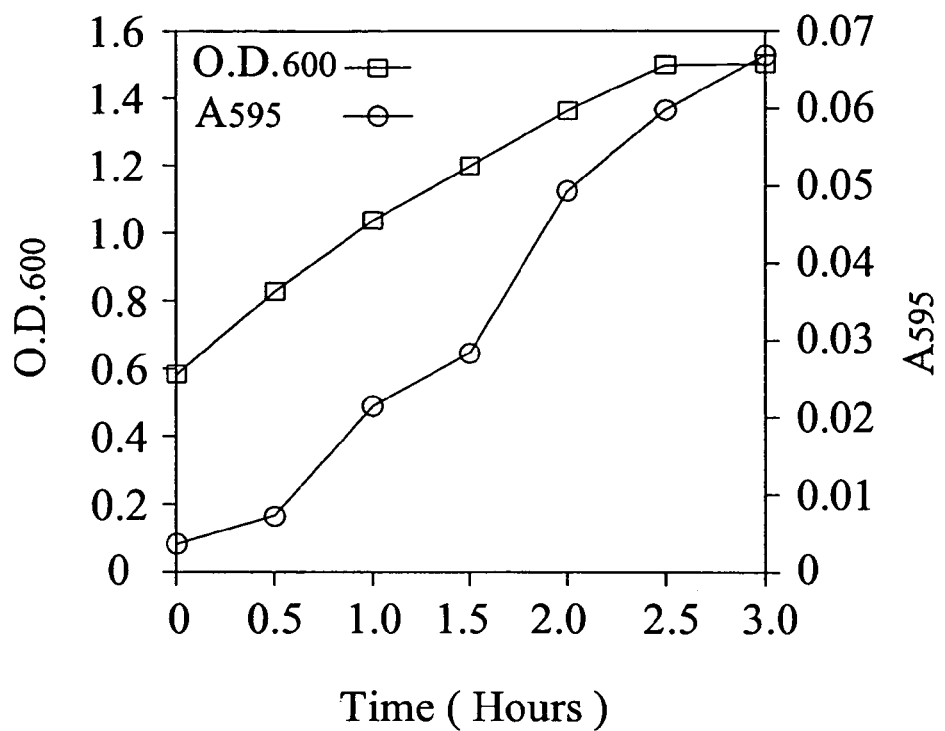
FIG. 23A is a photograph of Coomassie-stained His-tagged proteins from bacterial lysates recovered at various times post induction isolated using nickel (II) 3-[[[bis(carboxymethyl)amino]-acetyl]amino]-propyl magnetic silica particles.
FIG. 23 B is a graph of cell growth (as measured by $OD_{600}$) and protein concentration (as measured by $A_{595}$ of Coomassie stained proteins) as a function of time post-induction.
FIG. 23C is an SDS-PAGE gel of the purified protein in the samples.
Figure 23C:
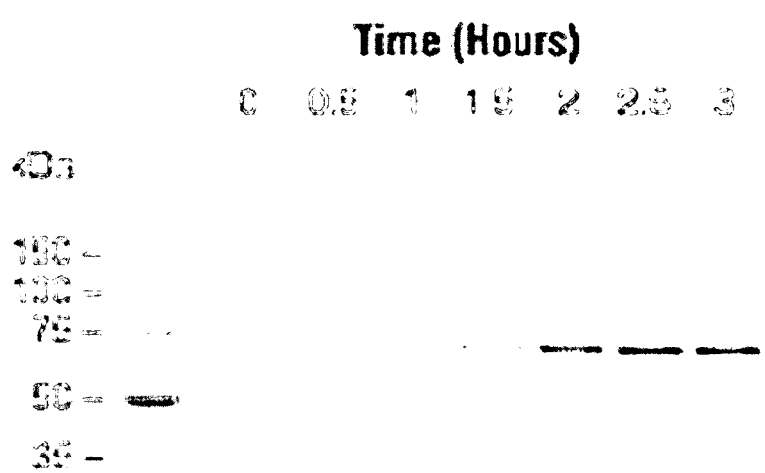

In a similar experiment, JM109 cells expressing His-methionyl tRNA synthetase were grown to an $OD_{600}$ and induced with 1 mM IPTG. Aliquots of the cultures were collected at half hour intervals through three hours post-induction, and used to prepare lysates that were treated as described above in the preceding paragraph. FIG. 23A is a photograph of eluted, Coomassie stained proteins, illustrating that recovery of labeled protein is positively correlated with the time post-induction. FIG. 23B is a graph plotting cell growth (as measured by $OD_{600}$) and protein concentration (as measured by $A_{595}$ of Coomassie stained proteins) as a function of time post-induction. FIG. 23C is an SDS-PAGE gel of the purified protein in the samples.

Figure 24:
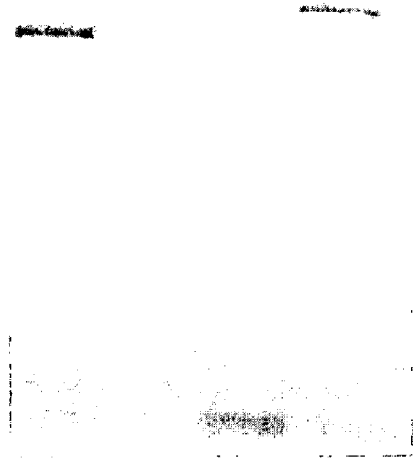
FIG. 24 shows a fluorescent image of an SDS-PAGE gel of his-tagged proteins isolated using nickel (II) 3-[[[bis(carboxymethyl)amino]-acetyl]amino]-propyl magnetic silica particles and stained with BODIPY.

Purified his-tagged proteins were contacted with nickel (II) 3-[[[Bis(carboxymethyl)amino]-acetyl]amino]-propyl magnetic silica particles and treated with BODIPY dye. The proteins/particles were separated by SDS-PAGE and visualized using fluorescent imager scanning (FIG. 24). With reference to FIG. 24, lane 1 contains His-firefly luciferase (62 kDa); lane 2 contains His-Renilla luciferase (36 kDa); lane 3 contains His-RNasin inhibitor (45 kDa); and lane 4 contains His-methionyl tRNA synthetase (76 kDa).

The experiment describes a method for quantitating proteins using in-particle labeling of proteins with dyes. Imidazole interferes with protein assays such as Bradford or BCA and must be removed by dialysis prior to measuring protein concentrations by those methods. In contrast, because imidazole not interfere with this assay, protein concentrations in samples can be evaluated directly without first dialyzing the samples.

Example 14

Method of Detecting Fluorescently Labeled Polypeptides

Figure 10:
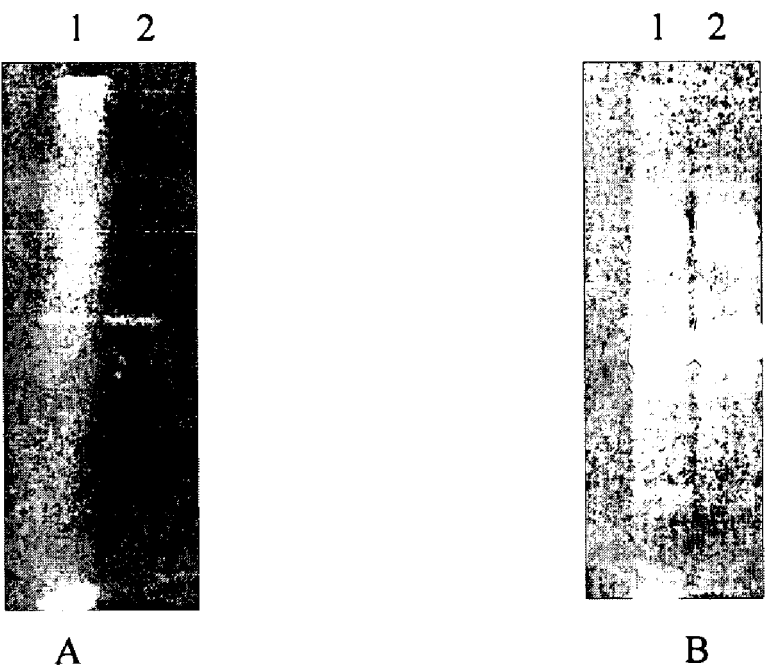
FIG. 10A shows an SDS-PAGE gel of fluorescently labeled his-tagged luciferase following fractionation by nickel (II) 3-[[[bis(carboxymethyl)amino]-acetyl]amino]-propyl magnetic silica particles.
FIG. 10B is an SDS-PAGE gel of fluorescently labeled his-tagged BSA following fractionation by copper—[[[bis(carboxymethyl)amino]-acetyl]amino]-propyl magnetic silica particles.

Copper (II) 3-[[[Bis(carboxymethyl)amino]-acetyl] amino]-propyl magnetic silica particles or nickel (II) 3-[[[Bis(carboxymethyl)amino]-acetyl]amino]-propyl magnetic silica particles were prepared as described above. The particles were washed once with 100 mM Hepes (pH 7.5). Aliquots (100 µl) of a bacterial lysate expressing his-luciferase or a BSA (10 mg/ml) in 100 mM Hepes (pH 7.5) were placed into separate Eppendorff tubes. A 50-µl aliquot of 10% (w/v) nickel (II) 3-[[[Bis(carboxymethyl)amino]-acetyl]amino]-propyl magnetic silica particles was added to the lysate in each tube and 50 µl 10% (w/v) copper (II) 3-[[[Bis(carboxymethyl)amino]-acetyl]amino]-propyl magnetic silica particles was added to the BSA in each tube and mixed by pipetting for 1-2 min. The particles were washed with 1 ml of 100 mM Hepes pH 7.5. Then, 100 µl of Fluorscein or Bodipy was dissolved in 60% Acetonitrile in 100 mM Hepes (pH 7.5) and added to the washed particles as well as to the control particles. The particles were washed 3× with 100 mM Hepes (pH 7.5) or until the free, unbound Fluorescein or Bodipy was removed. The bound polypeptides were eluted with 0.5 M imidazole. Polypeptides were detected by running the samples on SDS-PAGE followed by UV detection on a fluoroimager. As can be seen in FIG. 10A, his-luciferase labeled with Bodipy (lane 1) or Fluorescein (lane 2) was detectable. As can be seen in FIG. 10B, BSA labeled with Bodipy (lane 1) or Fluorescein (lane 2) was detectable.

The results indicate that proteins can be labeled with fluorescent dyes while the proteins are attached to the particles. This facilitates removal of free dye from the sample and affords rapid detection and quantitation of polypeptides.

Example 15

Figure 11:
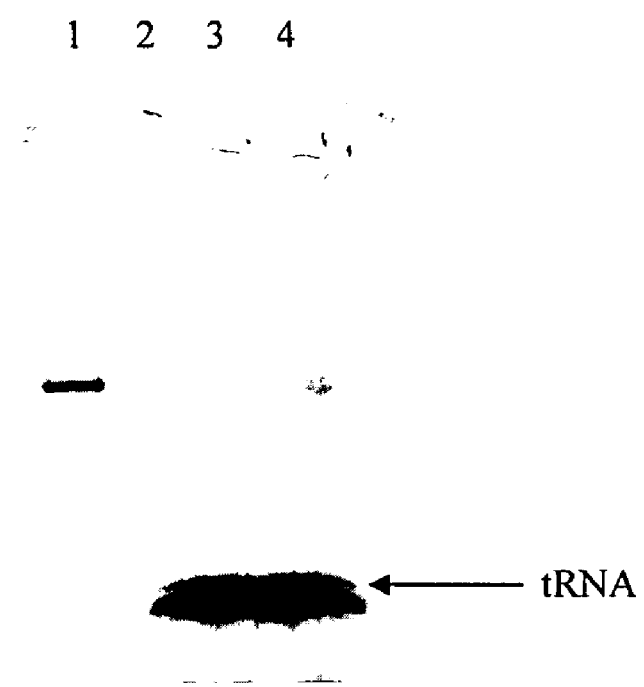
FIG. 11 is an SDS-PAGE gel of tRNA isolated using nickel (II) 3-[[[bis(carboxymethyl)amino]-acetyl]amino]-propyl magnetic silica particles.

Isolation of tRNA Synthetase Using Nickel (II) 3-[[[Bis (carboxymethyl)amino]-acetyl]amino]-propyl Magnetic Silica Particles Plasmid DNA encoding his-methionyl tRNA synthetase was expressed in an in vitro translation reaction in S-30 (Promega Corporation). The reaction mixtures contained 8 µg plasmid DNA, 5 µg Bodipy f-Met tRNA, amino acids (25 µl), S-30 premix (100 µl), and S-30 extract (75 µl). Reactions were performed at 37° C. for one hour. Each reaction mixture was combined with 3 mg of nickel (II) 3-[[[Bis (carboxymethyl)amino]-acetyl]amino]-propyl magnetic silica particles and mixed by pipetting. The particles were washed three times with 100 mM Hepes (pH 7.5). Material bound to the particles was eluted with 10 mM ammonium acetate. As a control, particles were contacted with the reaction mixture and washed, but not treated with ammonium acetate. The ammonium acetate eluate and the control particles were treated with 100 µl of a protein denaturation buffer and placed at 70° C. for 5 minutes, and analyzed by SDS-PAGE (FIG. 11). With reference to FIG. 11, lane 1 contains untreated lysate; lane 2 contains the flowthrough of lysate applied to the particles; lane 3 contains the ammonium acetate eluate; and lane 4 contains particles not treated with ammonium acetate. The results illustrate that tRNA binds tightly to the particles and that a portion of the tRNA can be eluted from the particles using an elution buffer containing 10 mM ammonium acetate.

Example 16

Purification of Cell-free Expressed His-tagged GFP

Prokaryotic in vitro transcription/translation reactions to express his-tagged GFP were conducted in 0.5 ml T7-S30 reaction volumes with 15 µg DNA template (pGFP-HIS) using the Rapid Translation System RT 500 (Roche) according to the manufacturer's instructions and incubated at 30° C. for 20 hours using the RTS 500 instrument (Roche). When used, FluoroTect™ or Bodipy®-fMet-tRNA was included at a concentration of 1 µg/50 µl of T7-S30 reaction.

The his-tagged GFP was purified by mixing the reaction mixtures with nickel (II) 3-[[[Bis(carboxymethyl)amino]-acetyl]amino]-propyl magnetic silica particles. The particles were washed twice with 100 mM Hepes (pH 7.5) and 10 mM imidazole. The particles were then washed with 30% methanol and eluted with 50% acetonitrile and 0.1% trifluoroacetic acid in water.

Figure 12:
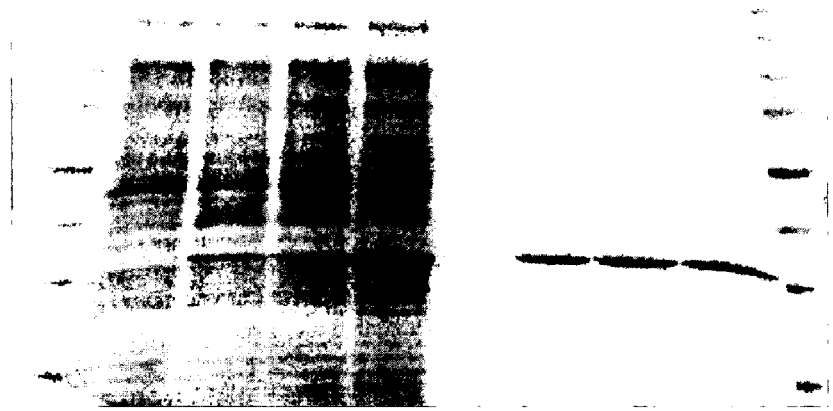
FIG. 12 is an SDS-PAGE gel of his-tagged proteins from a cell-free expression system isolated using nickel (II) 3-[[[bis(carboxymethyl)amino]-acetyl]amino]-propyl magnetic silica particles.
Figure 13:
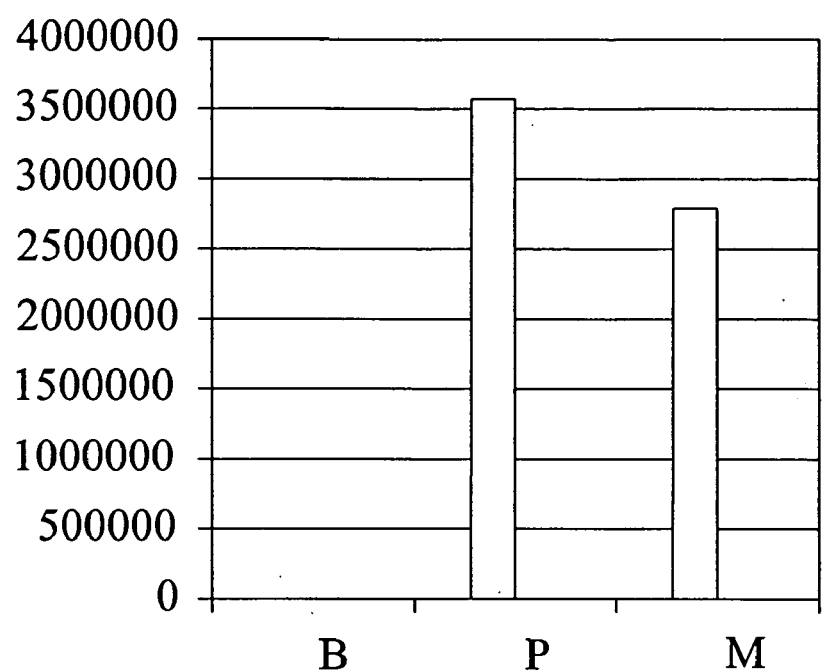
FIG. 13 is a graph comparing enzyme activity of free tRNA synthetase with that of tRNA synthetase bound to nickel (II) 3-[[[bis(carboxymethyl)amino]-acetyl]amino]-propyl magnetic silica particles.

The samples (5 µl, or in the case of wash or elution samples, 10 µl) were mixed with 20 µl of 4×SDS sample buffer and were run on 4-20% Novex Tris/Glycine gels, stained with Gel-Code and the fluorescent images captured with a digital camera (FIG. 12). With reference to FIG. 12, lanes 1 and 10 contain a size marker, lane 2 contains the S-30 lysate without DNA, lane 3 contains the S-30 lysate with plasmid DNA, lane 4 contains the S-30 lysate with plasmid DNA and Bodipy-fMet tRNA, lane 5 contains the S-30 lysate with plasmid DNA, lane 4 contains the S-30 lysate with plasmid DNA and fluorotect tRNA, lane 6 contains the S-30 lysate without plasmid DNA eluted with 0.1% trifluoroacetic acid in water, and lanes 7-9 contain S-30 lysate with plasmid DNA eluted with 50% acetonitrile and 0.1% trifluoroacetic acid in water.

The results indicate that nickel (II) 3-[[[Bis(carboxymethyl)amino]-acetyl]amino]-propyl magnetic silica particles can be used to purify his-tagged proteins expressed in cell free expression systems.

Example 17

In-particle Functional Assay of tRNA Synthetase Activity

The *E. coli* strain JM109 expressing his-methionyl tRNA synthetase was grown overnight at 37° C. in 50 ml LB medium containing tetracycline. A 15-ml aliquot of the overnight culture was added to 3 L LB medium and was grown at 37° C. When the culture reached the $OD_{600}$ between 0.4-0.6, IPTG was added to a final concentration of 1 mM and the cells were induced for at least 3 hours. Cells were pelleted by centrifugation and resuspended in 10 ml of 10 mM Hepes buffer (pH 8.0) and 5 mM $MgCl_2$ (buffer A). The sample was sonicated and pelleted by centrifugation. The supernatant containing his-methionyl tRNA synthetase was mixed with 10 ml of nickel (II) 3-[[[Bis(carboxymethyl)amino]-acetyl]amino]-propyl magnetic silica particles and incubated at 4° C. for 1 hr. The particles were washed five times with buffer A and used in the functional assay of bound tRNA synthetase, as described below. Unbound purified tRNA synthetase used in the assay was obtained by eluting bound protein from a sample of the particles with 0.5 M imidazole and dializing the eluate to remove the imidazole.

The activity of bound tRNA was assayed by incubating 84 µl of the particles containing bound methionyl tRNA synthetase, prepared as described in the preceding paragraph, 14.4 µl folic acid (0.01 M), 8.0 µl $^{35}S$ Met, 7.2 µl (2 M) NaCl, 12.0 µl (1 mM) Met, 144.0 µl (1 M) Hepes (pH 8.0), 14.4 µl (0.1 M) $MgCl_2$, 57.6 µl (0.1 M) ATP, 14.4 µl (0.01 M) CTP, 14.4 µl (0.1 M) DTT and 469.6 µl sterile double distilled water at 37° C. for 15 minutes. Included as a control was free his-methionyl tRNA synthetase prepared as described above. A 120 µl aliquot of 10% TCA was added and the mixtures incubated on ice for 15 minutes. The samples were filtered through 0.2 µm glass microtitre filters (Whatman), washed with 10% TCA, and washed with 10% ethanol. The filters were dried and counted in a scintillation counter. The results are presented in 13, which shows that the activity of the bound his-methionyl tRNA synthetase approaches that of the free, purified his-methionyl tRNA synthetase.

Example 18

Figure 14:
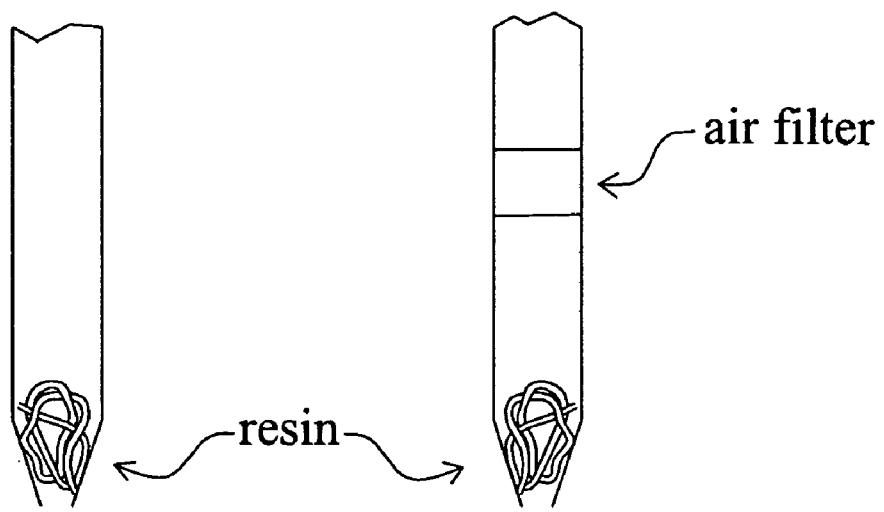
FIG. 14 shows pipette tips modified to include a solid support according to the present invention for use in purification and analysis of polypeptides.

Preparation of Proteins for Mass Spectrometer Analysis Using Modified Pipette Tips Pipette tips for mass spectrometer analysis are prepared using Promega 200 Barrier Tip 200-µl plastic pipette tips (Promega Corp., Madison, Wis.). The tips are loaded with 50-100 µl of nickel (II) 3-[[[Bis(carboxymethyl)amino]-acetyl]amino]-propyl magnetic silica particles or copper (II) 3-[[[Bis(carboxymethyl)amino-acetyl]amino]-propyl magnetic silica particles, prepared by modifying silica, as described above, using silica having a diameter in the range of 100 µm to 150 µm (Sigma-Aldrich Corp., Milwaukee, Wis.). The particles are introduced into pipette tips (FIG. 14). Prior to use, the particles in the tips are washed three times with 1 ml of 100 mM Hepes buffer (pH 7.5) with 10 mM imidazole. The pipette tips may include plastic or glass pipette tips having a capacity in the range of 10 µl to 1 ml. The amount of resin in the tip may be adjusted according the sample volume or the amount of protein to be purified.

Protein Purification/fractionation

For complex protein analysis, 5 µl of rabbit reticulocyte lysate (Promega) is mixed with 195 µl of 100 mM Hepes (pH 7.5). A 50 µl portion of the sample is transferred to a pipette tip, prepared as described above, containing 100 µl copper (II) 3-[[[Bis(carboxymethyl)amino]-acetyl]amino]-propyl magnetic silica particles. The sample is mixed by pipetting the sample into and out of the pipette tip 5 or 6 times. Proteins are allowed to bind to the particles by for 1-2 minutes. The particles are washed three times with 1 ml of 100 mM Hepes (pH 7.5). Bound proteins are eluted with 100 µl 0.1% TFA in water. The eluted samples are dried in Speed Vac and analyzed in a mass spectrometer (HT Laboratories).

To isolate his-tagged proteins, 50 µl of a bacterial lysate containing his-tagged proteins is transferred into a pipette tip containing 100 µl nickel (II) 3-[[[Bis(carboxymethyl)amino]-acetyl]amino]-propyl magnetic silica particles. The sample is mixed with the particles by pipetting in and out at least 5 or 6 times. The particles are washed three times with 1 ml binding buffer. The protein is eluted with 100 µl 0.1% TFA in water. The eluted samples are dried in Speed Vac and analyzed in a mass spectrometer (HT Laboratories).

Example 19

Sequential Multidimensional Polypeptide Fractionation and Separation Using Immobilized Metal Chelated Chromatography (IMAC)

Copper 3-[[[Bis(carboxymethyl)amino]-acetyl]amino]-propyl magnetic silica particles, cobalt 3-[[[Bis(carboxymethyl)amino]-acetyl]amino]-propyl magnetic silica particles, and zinc 3-[[[Bis(carboxymethyl)amino]-acetyl]amino]-propyl magnetic silica particles were prepared as described above. Gallium 3-[[[Bis(carboxymethyl)amino]-acetyl]amino]-propyl magnetic silica particles and iron 3[[[Bis(carboxymethyl)amino]-acetyl]amino]-propyl magnetic silica particles were prepared by removing the liquid from one-ml aliquots of 10% 3-[[[Bis(carboxymethyl)amino]acetyl]amino]-propyl magnetic silica particles by placing onto a magnetic stand, and adding 1 ml of 250 mM gallium (III) nitrate in water or 1 ml 250 mM iron (III) sulfate in water to the particles. The particles and metal solutions were mixed well by pipetting. The particles were separated from the metal solution by placing onto a magnetic stand and the metal solution removed. A second 1 ml aliquot of metal solution was mixed with the particles in each tube, incubated for 2 minutes, and the metal solution removed by placing onto a magnetic stand. The particles were washed four times with 1 ml MilliQ water, and then washed once with 100 mM Hepes (pH 7.5). Protein fractionation was performed as described below.

Binding and Elution of Complex Mixture of Proteins.

Figure 15:
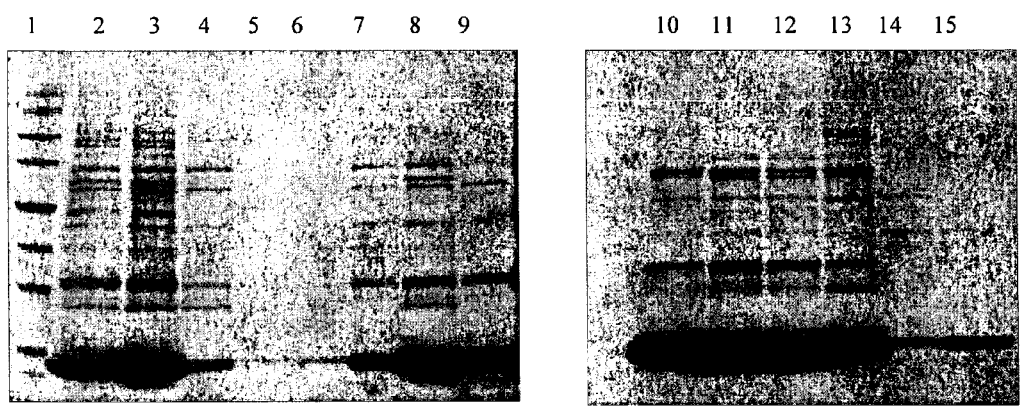
FIG. 15 is an SDS-PAGE gel illustrating binding and elution patterns of complex protein mixtures from rabbit reticulocyte lysate using various metal 3-[[[bis(carboxymethyl)amino]-acetyl]amino]-propyl magnetic silica particles.

Aliquots of rabbit reticulocyte lysate (5 µl) (Promega Corp.) were diluted with 195 µl of 100 mM Hepes (pH 7.5). Diluted lysate was mixed with 100 µl of 3-[[[Bis(carboxymethyl)amino]-acetyl]amino]-propyl magnetic silica particles or with nickel, cobalt, copper, zinc, iron, or gallium 3-[[[Bis(carboxymethyl)amino]-acetyl]amino]-propyl magnetic silica particles in Eppendorf tubes by pipetting for 1-2 minutes. The tubes were then placed onto a magnet, the supernatant was removed, and the particles washed three times with 1 ml of 100 mM Hepes (pH 7.5). Bound proteins were eluted from the particles with 0.5 M imidazole and were analyzed by SDS-PAGE (FIG. 15). Lane 1, size marker; lane 2, unfractionated rabbit reticulocyte lysate; lanes 3-9 flow through fractions from 3-[[[Bis(carboxymethyl)amino]-acetyl]amino]-propyl magnetic silica particles, nickel, cobalt, copper zinc, iron (III), or gallium (III) 3-[[[Bis(carboxymethyl)amino]-acetyl]amino]-propyl magnetic silica particles, respectively; lanes 10-16, imidazole eluate from 3-[[[Bis(carboxymethyl)amino]-acetyl]amino]-propyl magnetic silica particles, nickel, cobalt, copper zinc, iron (III), or gallium (III) 3-[[[Bis(carboxymethyl)amino]-acetyl]amino]-propyl magnetic silica particles, respectively. The results show that cobalt and copper 3-[[[Bis(carboxymethyl)amino]-acetyl]amino]-propyl magnetic silica particles bind relatively tightly to most proteins in the rabbit reticulocyte lysate under the conditions employed.

Figure 16A:
FIG. 16A is an SDS-PAGE gel illustrating binding and elution patterns of complex protein mixtures from rabbit reticulocyte lysate using copper 3-[[[bis(carboxymethyl)amino]-acetyl]amino]-propyl magnetic silica particles.
Figure 16B:
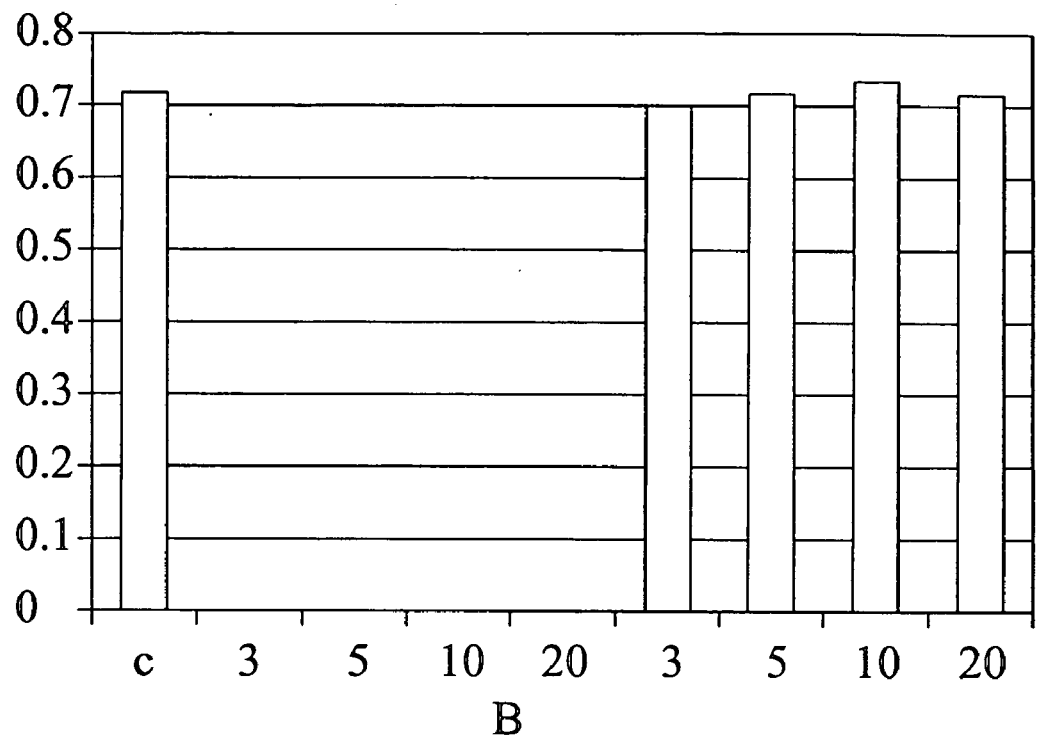
FIG. 16B is a graph showing protein concentrations ($A_{595}$ by Bradford method) of various fractions.

From 1-20 μl of rabbit reticulocyte lysate was combined with copper 3-[[[Bis(carboxymethyl)amino]-acetyl]amino]-propyl magnetic silica particles and processed as described above (FIG. 16A and 16B). Lane 1, size marker; lane 2, unfractionated rabbit reticulocyte lysate; lanes 3-6, flow through fraction from 3, 5, 10, or 20 μl of lysate, respectively, fractionated on copper 3-[[[Bis(carboxymethyl)amino]-acetyl]amino]-propyl magnetic silica particles; lanes 7-10, imidazole eluate from 3, 5, 10, or 20 μl of lysate on copper 3-[[[Bis(carboxymethyl)amino]-acetyl]amino]-propyl magnetic silica particles. The protein concentration for each fraction was determined by the Bradford method. FIG. 16B shows the absorbance (595 nm) of the flow through or eluate as a function of lysate volume fractionated.

Figure 17A:
FIG. 17A is an SDS-PAGE gel showing binding and elution patterns of complex protein mixtures from CHO cell lysate using copper 3-[[[bis(carboxymethyl)amino]-acetyl]amino]-propyl magnetic silica particles.
Figure 17B:
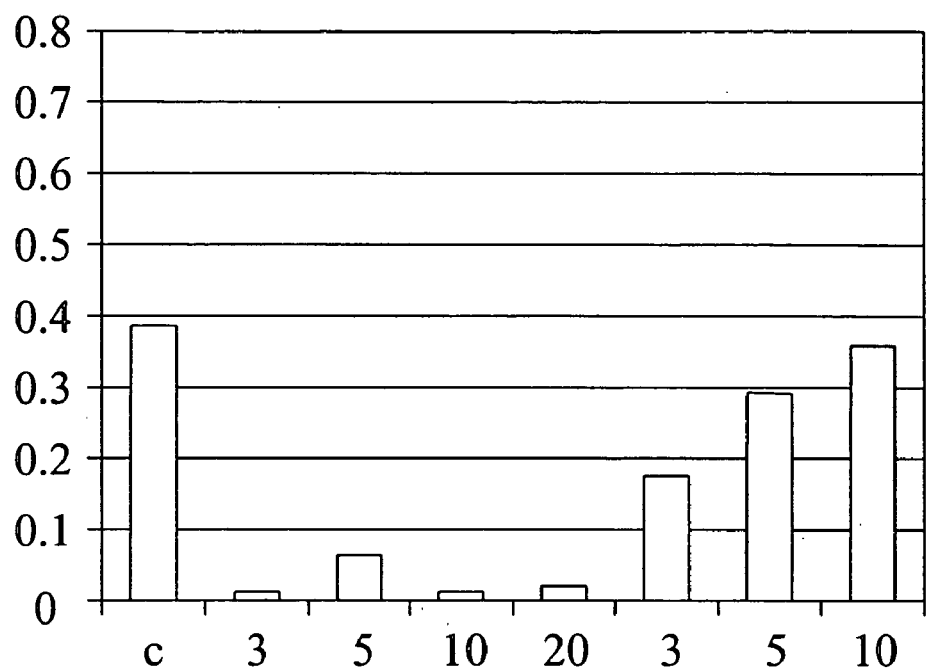
FIG. 17B is a graph showing protein concentrations ($A_{595}$ by Bradford method) of various fractions.

CHO cell lysate was prepared by suspending $8 \times 10^6$ cells in 1 ml of 100 mM Hepes (pH 7.5) and breaking the cells by freeze thawing. The cells were centrifuged, and the supernatant reserved. A supernatant aliquot of 100 μl was used for each experiment. Binding, washing, elution and analysis were done as explained for rabbit reticulocyte lysate. Results are shown in FIG. 17. With reference to FIG. 17A, lane 1 contains unfractionated CHO cell lysate; lane 4 contains protein molecular weight marker; lanes 2, 3, 5, and 6 contain flow through from 3, 5, 10 or 20, respectively; lanes 7-9 contain the imidazole eluate from 3, 5, or 10 μl CHO lysate.

Figure 18B:
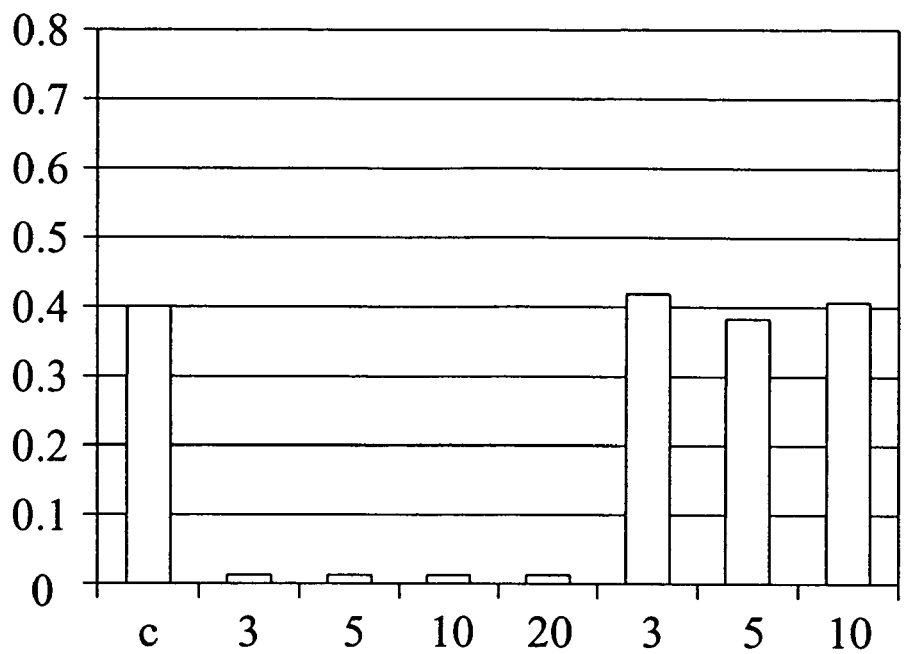
FIG. 18B is a graph showing protein concentrations ($A_{595}$ by Bradford method) of various fractions.

Wheat germ lysate (Promega) was also used for binding studies. 50 μl of wheat germ lysate was added to 50 μl of 100 mM Hepes (pH 7.5) buffer and was used for the experiment. Binding, washing, elution and analysis were done as explained for rabbit reticulocyte lysate. Results are shown in FIG. 18.

Sequential Multidimensional Separation of Proteins

Figure 19:
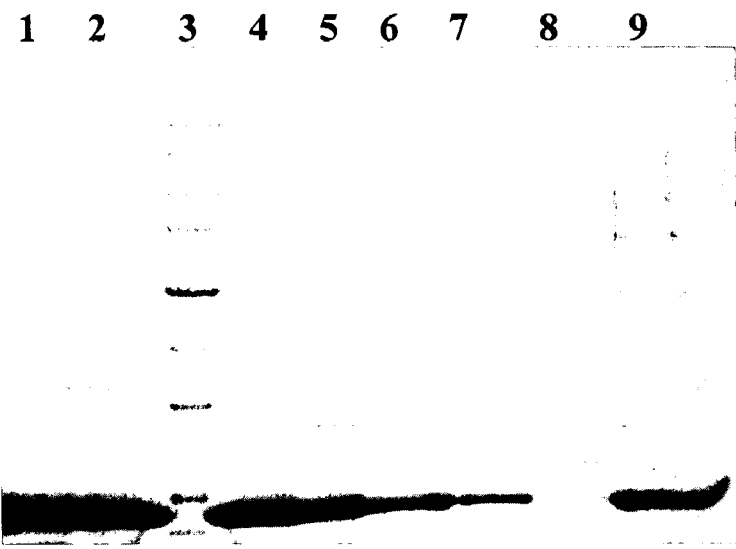
FIG. 19 is an SDS-PAGE gel illustrating sequential elution of proteins with copper 3-[[[bis(carboxymethyl)amino]-acetyl]amino]-propyl magnetic silica particles under various conditions.

Aliquots of rabbit reticulocyte lysate (5 μl) (Promega Corp.) were diluted with 195 μl of 100 mM Hepes (pH 7.5). Diluted lysate was mixed with 100 μl copper 3-[[[Bis(carboxymethyl)amino]-acetyl]amino]-propyl magnetic silica particles in Eppendorf tubes by pipetting for 1-2 minutes. The tubes were then placed onto a magnet, the supernatant was removed, and the particles washed three times with 1 ml of 100 mM Hepes (pH 7.5). Proteins were eluted by sequentially treating the particles with 1, 5, 10, 20 and 50% acetonitrile. The particles were then treated with double distilled water, followed by eluting with 0.1 and 1% trifluoroacetic acid (TFA). All these samples were analyzed by SDS-PAGE. Results are shown in FIG. 19.

Figure 20:
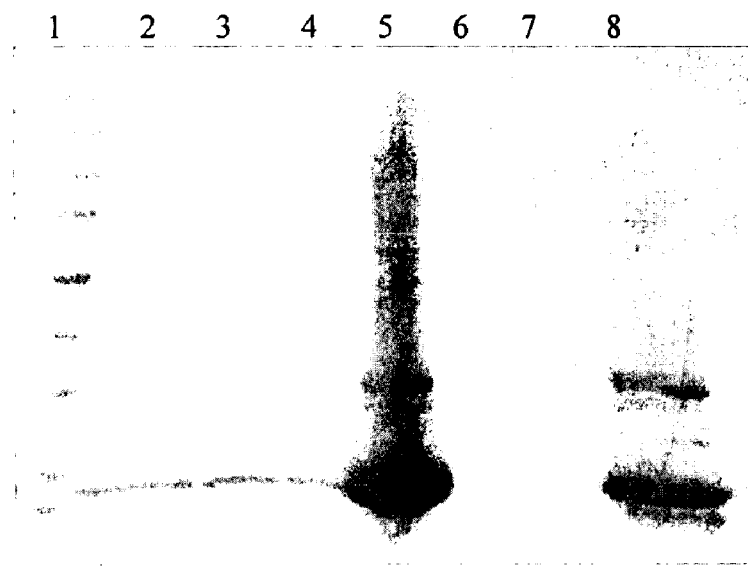
FIG. 20 is an SDS-PAGE gel illustrating sequential elution of proteins with copper 3-[[[bis(carboxymethyl)amino]-acetyl]amino]-propyl magnetic silica particles under various conditions.

In a separate experiment, proteins were first eluted with 100, 200, 500 or 1000 mM imidazole, followed by the elution of the same particles with buffers of pH 8.5, 9.5, 10.5, or 12.5. Samples were analyzed by SDS-PAGE and results are shown in FIG. 20.

Example 20

Separation of Phosphoproteins

Iron (III) and gallium (III) 3-[[[Bis(carboxymethyl)amino]-acetyl]amino]-propyl magnetic silica particles, prepared as described above, were equilibrated with 100 mM Hepes (pH 7.5).

Figure 21:
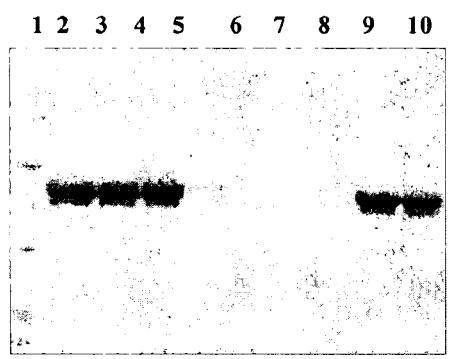
FIG. 21 is an SDS-PAGE gel of the phosphoprotein ovalbumin isolated using iron (III) or gallium (III) 3-[[[bis(carboxymethyl)amino]-acetyl]amino]-propyl magnetic silica particles.
Figure 22:
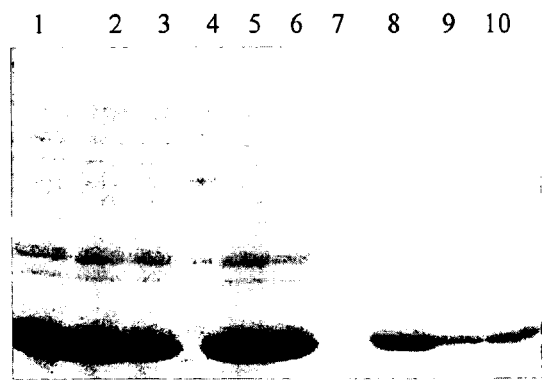
FIG. 22 is an SDS-PAGE gel of phosphoproteins isolated from rabbit reticulocyte lysate using iron (III) or gallium (III) 3-[[[bis(carboxymethyl)amino]-acetyl]amino]-propyl magnetic silica particles.

A solution of ovalbumin (Sigma) containing 10 mg/ml in 100 mM Hepes (pH 7.5) was prepared. Aliquots (100 μl) of the solution were added to Iron (III) and gallium (III) 3-[[[Bis(carboxymethyl)amino]-acetyl]amino]-propyl magnetic silica particles and mixed well by pipetting. Nickel (II) 3-[[[Bis(carboxymethyl)amino]-acetyl]amino]-propyl magnetic silica particles and uncharged 3-[[[Bis(carboxymethyl)amino]-acetyl]amino]-propyl magnetic silica particles were included as controls. After binding, particles were washed three times with 100 mM Hepes (pH 7.5) buffer. Bound protein was eluted using 2% ammonium hydroxide. The samples were analyzed by SDS-PAGE (FIG. 21). In parallel experiments, rabbit reticulocyte (diluted 1:1 with 100 mM Hepes (pH 7.5)) was used, and the fractions analyzed by SDS-PAGE (FIG. 22).

Example 21

Screening Expression Libraries for Membrane Proteins

The method of isolation of membrane proteins described in Examples 7 and 8, above, will be used to screen libraries for expression of membrane proteins. Pools of c-DNA clones (50-100 clones per pool) will be used as templates for small-scale transcription/translation reactions to generate proteins in presence of canine or HeLa microsomal membrane in a 96 well format. Amine-modified silica magnetic particles will be added to the reaction mix to capture the membrane vesicles and any associated membrane proteins.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

The invention claimed is:

1. A method for isolating target material from a starting material comprising:
   (a) contacting the starting material with a composition selected from the group consisting of:

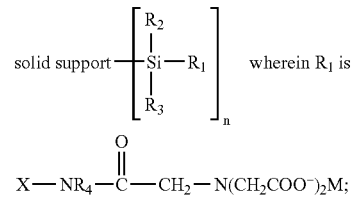

$$X-NR_4-\overset{O}{\underset{\|}{C}}-CH_2-N(CH_2COO^-)_2M;$$

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an integer $\geq 1$; and

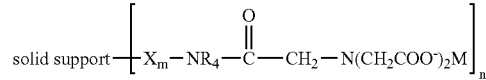

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

M is a metal ion;

n is an integer $\geq 1$; and m is 0 or 1;

to form a complex between at least a portion of the target material and the composition.

2. The method of claim 1, wherein X is $-(CH_2)_3-$, $R_4$ is H, and M is Ni(II).

3. The method of claim 1, further comprising:
   (b) washing the complex of step (a); and
   (c) eluting the target material.

4. The method of claim 1, wherein the target material is selected from the group consisting of polypeptide, a polynucleotide, and an endotoxin.

5. The method of claim 1, wherein the target material is a polypeptide.

6. The method of claim 5, wherein the polypeptide comprises an affinity tag.

7. The method of claim 6, wherein the affinity tag comprises a polyhistidine tag.

8. The method of claim 5, wherein the polypeptide comprises a detectable label.

9. The method of claim 8, wherein the detectable label is selected from the group consisting of a fluorophore and a dye, a combination thereof.

10. The method of claim 1, wherein the starting material comprises a protein, further comprising:
    (b) contacting the complex of step (a) with a protein-complexing detectable label to form a labeled protein complex;
    (c) washing the support to remove uncomplexed label;
    (d) detecting the labeled protein complex.

11. The method of claim 10, further comprising:
    (e) measuring complexed label; and
    (f) determining the concentration of the protein by correlating the amount of complexed label of step (e) with a known quantity of labeled protein complex.

12. The method of claim 10, wherein the detectable label is selected from the group consisting of a fluorophore and a dye, or a combination thereof.

13. A method for separating target material from non-target material in a starting material comprising:
    (a) contacting the starting material with a composition under conditions suitable to form a complex between the composition and non-target material, the composition comprising:

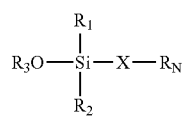

wherein X is a substituted or unsubstituted alkylene moiety, a substituted or unsubstituted aralkylene moiety, or a substituted or unsubstituted arylene moiety;

$R_1$ is a hydrocarbon moiety, or a substituted hydrocarbon moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety, or a substituted hydrocarbon moiety; and $R_N$ is $NH_2$, $NHR_{N1}$, $NR_{N1}R_{N2}$, or $NR_{N1}R_{N2}R_{N3}$, wherein $R_{N1}$, $R_{N2}$, and $R_{N3}$ are independently selected from a hydrocarbon moiety with up to a six-carbon main chain, a substituted hydrocarbon moiety with up to a six-carbon main chain, or a hydrogen atom;

(b) collecting the flow through comprising target material;

(c) contacting the target material of step (b) with a second composition under conditions suitable to form a complex between the support and the target material, the second composition selected from the group consisting of

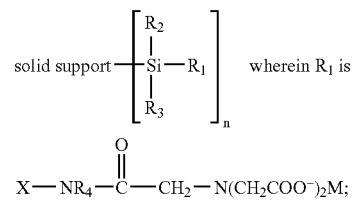

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an integer $\geq 1$; and

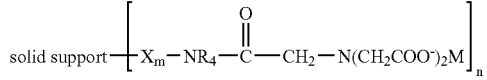

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

M is a metal ion;

n is an interger $\geq 1$; and m is 0 or 1.

14. The method of claim 13, wherein the solid support is selected from the group consisting of silica and magnetic silica particles.

15. The method of claim 13, wherein the support of step (c) reversibly binds the target material.

16. The method of claim 13, wherein the target material is selected from the group consisting of a polypeptide, a nucleic acid, and an endotoxin.

17. A method for separating nucleic acids from a starting material:
    (a) contacting the starting material with a composition under suitable conditions to form a complex between the nucleic acid and the composition, the composition selected from the group consisting of

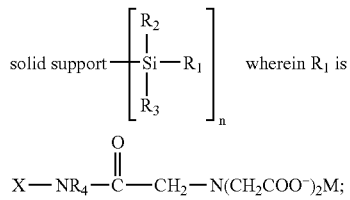

$$X-NR_4-\overset{O}{\underset{\|}{C}}-CH_2-N(CH_2COO^-)_2M;$$

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an interger $\geq 1$ and

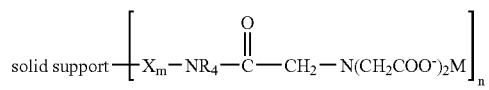

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

M is a metal ion;

n is an interger $\geq 1$; and m is 0 or 1.

18. The method of claim 17 further comprising:

(b) eluting the nucleic acid of step (a).

19. The method of claim 17, wherein the nucleic acid comprises tRNA.

20. The method of claim 17, wherein the metal ion is nickel.

21. A method for assaying the activity of an enzyme in a starting material, the enzyme capable of catalyzing the conversion of a substrate to a product, comprising:

(a) contacting the starting material with a composition to form a complex between the enzyme and the composition, the composition selected from the group consisting of

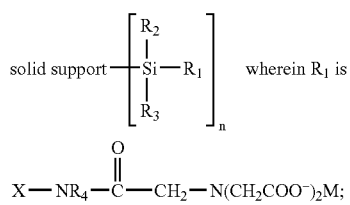

$$X-NR_4-\overset{O}{\underset{\|}{C}}-CH_2-N(CH_2COO^-)_2M;$$

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an interger $\geq 1$; and

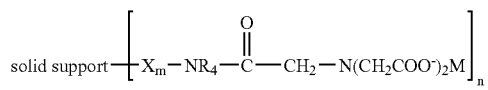

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

M is a metal ion;

n is an interger $\geq 1$; and m is 0 or 1;

(b) contacting under suitable reaction conditions the complex of step (a) with a substrate for the enzyme; and (c) detecting a decrease in substrate or an increase in product.

22. The method of claim 21, wherein the enzyme comprises a polyhistidine tag.

23. A method for separating phosphoproteins from a starting material comprising:

(a) contacting the starting material with a composition to form a complex between the phosphoprotein and the composition, the composition selected from the group consisting of

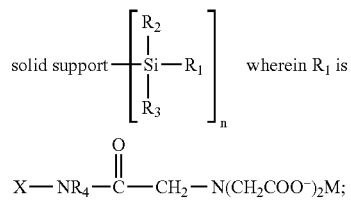

$$X-NR_4-\overset{O}{\underset{\|}{C}}-CH_2-N(CH_2COO^-)_2M;$$

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an interger $\geq 1$; and

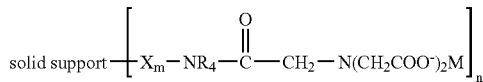

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

M is a metal ion;

n is an interger $\geq 1$; and m is 0 or 1;

wherein the metal ion is selected from the group consisting of iron (III) or gallium (III).

24. A method for sequential fractionation of polypeptides in a starting material having at least least two different types of polypeptides comprising:

(a) contacting the starting material with a composition to form a complex between the polypeptides and the composition, the composition selected from the group consisting of

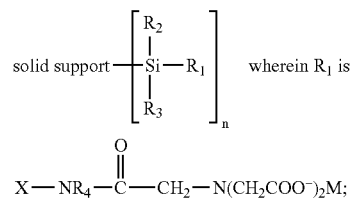

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom;

M is a metal ion; and n is an interger $\geq 1$ and

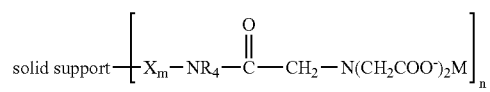

wherein X is a substituted or unsubstituted alkylene moiety, a substituted or unsubstituted aralkylene moiety, or a substituted or unsubstituted arylene moiety;

$R_4$ is a hydrocarbon moiety, a substituted hydrocarbon moiety, or a hydrogen atom;

M is a metal ion;

n is an interger $\geq 1$; and m is 0 or 1;

wherein the metal ion is selected from the group consisting of copper and cobalt, to form a complex between the polypeptides and the composition; and (b) sequentially eluting the polypeptides by contacting the complex with at least one elution buffer that achieves an effect selected from the group consisting of altering the pH, altering the concentration of at least one salt, providing an organic solvent, altering ionic conditions, altering hydrophobic conditions, and providing a chelating agent, or combinations thereof.

* * * * *

UNITED STATES PATENT AND TRADEMARK OFFICE
CERTIFICATE OF CORRECTION

PATENT NO.        : 7,354,750 B2
APPLICATION NO. : 10/689368
DATED             : April 8, 2008
INVENTOR(S)       : Daniel J. Simpson et al.

It is certified that error appears in the above-identified patent and that said Letters Patent is hereby corrected as shown below:

Column 29, Claim 9, line 27, insert --or-- after the comma "," and before the word "a".
Column 30, Claim 13, line 54, "interger" should read --integer--.
Column 31, Claim 17, line 28, "interger" should read --integer--.
Column 31, Claim 17, line 41, "interger" should read --integer--.
Column 32, Claim 21, line 15, "interger" should read --integer--.
Column 32, Claim 21, line 29, "interger" should read --integer--.
Column 33, Claim 23, line 2, "interger" should read --integer--.
Column 33, Claim 23, line 16, "interger" should read --integer--.
Column 34, Claim 24, line 12, "interger" should read --integer--.
Column 34, Claim 24, line 27, "interger" should read --integer--.

Signed and Sealed this

Twelfth Day of August, 2008

JON W. DUDAS
*Director of the United States Patent and Trademark Office*